(12) United States Patent
Wu et al.

(10) Patent No.: US 11,396,507 B2
(45) Date of Patent: Jul. 26, 2022

(54) SALTS OF A COMPOUND AND THE CRYSTALLINE FORMS THEREOF

(71) Applicant: HUTCHISON MEDIPHARMA LIMITED, Shanghai (CN)

(72) Inventors: Zhenping Wu, Shanghai (CN); Wenji Li, Shanghai (CN); Ling Feng, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 0 days.

(21) Appl. No.: 16/641,054

(22) PCT Filed: Aug. 22, 2018

(86) PCT No.: PCT/CN2018/101699
§ 371 (c)(1),
(2) Date: Feb. 21, 2020

(87) PCT Pub. No.: WO2019/037737
PCT Pub. Date: Feb. 28, 2019

(65) Prior Publication Data
US 2021/0047318 A1 Feb. 18, 2021

(30) Foreign Application Priority Data
Aug. 22, 2017 (CN) .......................... 201710723169.3

(51) Int. Cl.
*C07D 471/04* (2006.01)
(52) U.S. Cl.
CPC ................. *C07D 471/04* (2013.01)
(58) Field of Classification Search
CPC .................................................. C07D 471/04
USPC ........................................................ 514/234
See application file for complete search history.

(56) References Cited

U.S. PATENT DOCUMENTS 9,434,726 B2 * 9/2016 Su .......................... C07D 471/04
10,052,330 B2 * 8/2018 Su ............................ A61P 11/02

FOREIGN PATENT DOCUMENTS

WO WO2012167733 12/2012
WO WO-2012167733 A1 * 12/2012 ............... A61P 29/00

OTHER PUBLICATIONS

Stephen Berge etal, Phamaceutical Salts. (Year: 1977).*
International Preliminary Report on Patentability of International Application PCT/CN2018/101699, dated Feb. 25, 2020, 7 pages.
International Search Report and Written Opinion of International Application PCT/CN2018/101699, prepared by the International Searching Authority, dated Oct. 16, 2018, 11 pages.
Bastin, "Salt Selection and Optimized Procedures for Pharmaceutical New Chemical Entities", Organic Process and Research Development, vol. 4, No. 5, pp. 427-435 (2000).
Berge, et al., "Pharmaceutical Salts," Journal of Pharmaceutical Sciences, vol. 66(1), p. 1-19,(1977).
Caira, et al., "Crystalline Polymorphism of Organic Compounds," *Topics in Current Chemistry*, vol. 198, p. 163-203, (1998).

* cited by examiner

*Primary Examiner* — Taofiq A Solola
(74) *Attorney, Agent, or Firm* — Hoxie & Associates LLC

(57) ABSTRACT

The present invention belongs to the pharmaceutical field, and provides the pharmaceutically acceptable salts of the compound (S)-7-(4-(1-(methylsulfonyl)piperidin-4-yl)phenyl)-N-(morpholin-2-ylmethyl)pyrido[3,4-b]pyrazin-5-amine and the crystalline forms thereof, the solvates and the crystalline forms thereof, the pharmaceutical compositions comprising the same as well as the methods of preparing the same and the use thereof.

21 Claims, 10 Drawing Sheets

SALTS OF A COMPOUND AND THE CRYSTALLINE FORMS THEREOF

CROSS REFERENCE TO RELATED APPLICATIONS

This application is a United States Application under 35 U.S.C. 371 claiming benefit of PCT Application No. PCT/CN2018/101699, filed on Aug. 22, 2018, which claims the benefit of Chinese Patent Application No. 201710723169.3, filed on Aug. 22, 2017, the contents of each of which are incorporated herein by reference.

Field of the Invention

The present invention belongs to the pharmaceutical field, and provides the pharmaceutically acceptable salts of the compound (S)-7-(4-(1-(methylsulfonyl)piperidin-4-yl) phenyl)-N-(morpholin-2-ylmethyl)pyrido[3,4-b]pyrazin-5-amine and the crystalline forms thereof, the solvates and the crystalline forms thereof, the pharmaceutical compositions comprising the same as well as the methods of preparing the same and the use thereof.

BACKGROUND OF THE INVENTION

Spleen Tyrosine Kinase (Syk) is a non-receptor tyrosine kinase that plays critical roles in immunoreceptor- and integrin-mediated signaling in a variety of cell types, including B cells, macrophages, monocytes, mast cells, eosinophils, basophils, neutrophils, dendritic cells, T cells, natural killer cells, platelets, and osteoclasts.

Syk is essential for B-cell activation through B-cell receptor (BCR) signaling. Syk becomes activated upon binding to phosphorylated BCR and thus initiates the B-cell receptor signaling. B-cell receptor signaling can lead to a wide range of biological effects, which signaling in turn depends on the developmental stage of the B-cell. The magnitude and duration of BCR signals must be precisely regulated. Aberrant BCR-mediated signaling can cause disregulated activation or the formation of pathogenic auto-antibodies leading to multiple autoimmune or inflammatory diseases. Mice tacking Syk show impaired maturation of B-cells, diminished immunoglobulin production, compromised T-cell-independent immune responses, and marked attenuation of the calcium ion sign upon BCR stimulation.

A large body of evidences support the important role of B-cells and the humoral immune system in the pathogenesis of autoimmune and inflammatory diseases. Auto-antibodies and their resulting immune complexes are known to play pathogenic roles in autoimmune disease and inflammatory disease. The pathogenic response to these antibodies is dependent on signaling through Fe Receptors, which is, in turn, mediated by Syk activation. Because of Syk's role in B-cell activation, as well as Fe dependent signaling, inhibitors of Syk can be useful as inhibitors of B-cell mediated pathogenic activity, including autoantibody production. Therefore, inhibition of Syk enzymatic activity in cells is useful as a treatment for autoimmune disease through its inhibitory effects on autoantibody production.

Thus, the inhibition of Syk activity can be useful for the treatment of autoimmune diseases and inflammatory diseases, such as: systemic lupus erythematosus, rheumatoid arthritis, Sjorgen's syndrome, IgA nephropathy, autoimmune hemolytic anemia, multiple sclerosis, idiopathic thrombocytopenic purpura, myasthenia gravis, allergic rhinitis, chronic obstructive pulmonary disease, adult respiratory distress syndrome, and asthma. In addition, Syk has been reported to play an important role in ligand-independent signaling through the B-cell receptor, known to be an important survival signal in B-cells. Thus, inhibition of Syk activity is useful in treating cancer, preferably hematological malignancy such as: lymphoma, leukemia, and multiple myeloma.

The relevant compound (S)-7-(4-(1-(methylsulfonyl)piperidin-4-yl)phenyl)-N-(morpholin-2-ylmethyl)pyrido[3,4-b]pyrazin-5-amine of the present invention has the effect of effectively inhibiting Syk kinase activity. Thus, it is useful in treating diseases responsive to inhibition of Syk kinase activity, such as the treatment of autoimmune diseases, inflammatory diseases, and cancer.

The phenomenon that a compound could exist in two or more crystal structures is known as polymorphism. Many compounds may exist as various polymorph crystals and also in a solid amorphous form. Until polymorphism of a compound is discovered, it is highly unpredictable (1) whether a particular compound will exhibit polymorphism, (2) how to prepare any such unknown polymorphs, and (3) how are the properties, such as stability, of any such unknown polymorphs. See, e.g., J. Bernstein "Polymorphism in Molecular Crystals", Oxford University Press, (2002).

Forming a salt will not change the biological activity of the compound itself, but can change the physical and chemical properties of the compound, such as solubility, stability, crystallinity, polymorphism, and the like. However, it is unpredictable which specific properties will change and how is the degree of the change. It is also unpredictable whether a compound or the salt formed with an acid/base can exist as crystalline or amorphous forms, which crystalline form will be formed, how to get a crystalline form, and whether the formed crystalline forms have a particular property.

Since the properties of a solid material depend on the structure as well as on the nature of the compound itself, different solid forms of a compound can and often do exhibit different physical and chemical properties as well as different biopharmaceutical properties. Differences in chemical properties can be determined, analyzed and compared through a variety of analytical techniques. Those differences may ultimately be used to differentiate among different solid forms. Furthermore, differences in physical properties, such as solubility, and biopharmaceutical properties, such as bioavailability, are also of importance when describing the solid state of a pharmaceutical compound. Similarly, in the development of a pharmaceutical compound, e.g., (S)-7-(4-(1-(methylsulfonyl)piperidin-4-yl)phenyl)-N-(morpholin-2-ylmethyl)pyrido[3,4-b]pyrazin-5-amine, the salts, new crystalline and amorphous forms of the pharmaceutical compound are also of importance.

The compound (S)-7-(4-(1-(methylsulfonyl)piperidin-4-yl)phenyl)-N-(morpholin-2-yl methyl)pyrido[3,4-b]pyrazin-5-amine as well as the preparation thereof was described in patent application WO2012167733A1.

Contents of the Invention

SUMMARY

Upon extensive explorations and researchs, we have found that the compound (S)-7-(4-(1-(methytsulfonyl)piperidin-4-yl)phenyl)-N-(morpholin-2-ylmethyl)pyrido[3,4-b]pyrazin-5-amine can be prepared into various pharmaceutically acceptable salts, with the chemical structure of Formula A. Studies have shown that, compared with its free base, the solubility of salt of Formula A is significantly increased, which is beneficial for improving the pharmacokinetic characteristics and in vivo bioavailability of the compound. We have also found that salt of Formula A can exist in different crystalline forms (i.e. polymorphs), and can form solvates with certain solvents. We have made extensive studies on the polymorphs of salt of Formula A and have finally prepared and determined the crystalline forms which meet the requirement of pharmaceutical use. Based on these studies, the present invention provides the various crystalline forms of the pharmaceutically acceptable salts of the compound (S)-7-(4-(1-(methylsulfonyl)piperidin-4-yl)phenyl)-N-(morpholin-2-ylmethyl)pyrido[3,4-b]pyrazin-5-amine and the solvates and the crystalline forms thereof, which are designated as Form A-I, form B-I, Form B-II, Form B-III, Form C-I, Form C-II, and B-III respectively.

Formula A

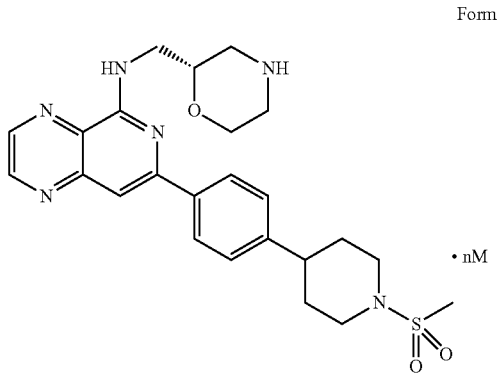

wherein, n is 0.5 or 1;

M is the pharmaceutically acceptable acid molecule.

In one aspect, the polymorphs of salt of Formula. A or the solvates thereof provided by the present invention have good crystallinity, high solubility, and good stability.

Firstly, the present invention provides the pharmaceutically acceptable salts of (S)-7(4-(1-(methylsulfonyl)piperidin-4-yl)phenyl)-N-(morpholin-2-ylmethyl)pyrido[3,4-b]pyrazin-5-amine.

Secondly, the present invention provides the pharmaceutically acceptable salts of (S)-7-(4-(1-(methylsulfonyl)piperidin-4-yl)phenyl)-N-(morpholin-2-ylmethyl)pyrido[3,4-b]pyrazin-5-amine of Formula A, i.e. salt of Formula A.

Further, the present invention provides the pharmaceutically acceptable salts of (S)-7-(4-(1-(methylsulfonyl)piperidin-4-yl)phenyl)-N-(morpholin-2-ylmethyl)pyrido[3,4-b]pyrazin-5-amine of Formula A, which are acetate, p-Tosylate, and malate respectively.

Even further, the present invention provides the pharmaceutically acceptable salts of (S)-7-(4-(1-(methylsulfonyl)piperidin-4-yl)phenyl)-N-(morpholin-2-ylmethyl)pyrido[3,4-b]pyrazin-5-amine of Formula A, which are monoacetate, mono p-Tosylate, monomalate, and hemimalate respectively.

Even further, the present invention provides crystalline Form A-I of (S)-7-(4-(1-(methylsulfonyl)piperidin-4-yl)phenyl)-N-(morpholin-2-ylmethyl)pyrido[3,4-b]pyrazin-5-amine monoacetate, i.e. Form A-I of salt of Formula A (wherein, n is 1, M is acetic acid).

Even further, the present invention provides crystalline Form B-I of (S)-7-(4-(1-(methylsulfonyl)piperidin-4-yl)phenyl)-N-(morpholin-2-ylmethyl)pyrido[3,4-b]pyrazin-5-amine mono p-Tosylate, i.e. Form B-I of salt of Formula A (wherein, n is 1, M is p-toluenesulfonic acid).

Even further, the present invention provides crystalline Form B-II of (S)-7-(4-(1-(methylsulfonyl)piperidin-4-yl)phenyl)-N-(morpholin-2-ylmethyl)pyrido[3,4-b]pyrazin-5-amine mono p-Tosylate, i.e. Form B-II of salt of Formula A (wherein, n is 1, M is p-toluenesulfonic acid).

Even further, the present invention provides the solvate of (S)-7-(4-(1-(methylsulfonyl)piperidin-4-yl)phenyl)-N-(morpholin-2-ylmethyl)pyrido[3,4-b]pyrazin-5-amine p-Tosylate, which is hydrate of salt of Formula A (wherein, n is 1, M is p-toluenesulfonic acid).

Even further, the present invention provides hydrate of (S)-7-(4-(1-(methylsulfonyl)piperidin-4-yl)phenyl)-N-(morpholin-2-ylmethyl)pyrido[3,4-b]pyrazin-5-amine p-Tosylate, which is hemihydrate of salt of Formula A (wherein, n is 1, M is p-toluenesulfonic acid).

Even further, the present invention provides hydrate of (S)-7-(4-(1-(methylsulfonyl)piperidin-4-yl)phenyl)-N-(morpholin-2-ylmethyl)pyrido[3,4-b]pyrazin-5-amine p-Tosylate, which is hemihydrate of salt of Formula A (wherein, n is 1, M is p-toluenesulfonic acid), which is Form B-III.

Even further, the present invention provides crystalline Form C-I of (S)-7-(4(1-(methylsulfonyl)piperidin-4-yl)phenyl)-N-(morpholin-2-ylmethyl)pyrido[3,4-b]pyrazin-5-amine monomalate, i.e. Form C-I of salt of Formula A (wherein, n is 1, M is malic acid).

Even further, the present invention provides the solvate of (S)-7-(4-(1-(methylsulfonyl)piperidin-4-yl)phenyl)-N-(morpholin-2-ylmethyl)pyrido[3,4-b]pyrazin-5-amine malate, which is hydrate of salt of Formula A (wherein, n is 0.5, M is malic acid).

Even further, the present invention provides hydrates of (S)-7-(4-(1-(methylsulfonyl)piperidin-4-yl)phenyl)-N-(morpholin-2-ylmethyl)pyrido[3,4-b]pyrazin-5-amine malate, which are hydrate containing 0.75 molecule of water, and monohydrate of salt of Formula A (wherein, n is 0.5, M is malic acid).

Even further, the present invention provides hydrate of (S)-7-(4-(1-(methylsulfonyl)piperidin-4-yl)phenyl)-N-morpholin-2-ylmethyl)pyrido[3,4-b]pyrazin-5-amine malate, which is hydrate containing 0.75 molecule of water of salt of Formula A (wherein, n is 0.5, M is malic acid), which is Form C-II.

Even further, the present invention provides hydrate of (S)-7-(4-(1-(methylsulfonyl)piperidin-4-yl)phenyl)-N-morpholin-2-ylmethyl)pyrido[3,4-b]pyrazin-5-amine malate, which is monohydrate of salt of Formula A (wherein, n is 0.5, M is malic acid), which is Form C-III.

In another aspect, the present invention provides the methods of preparation for salt of Formula A or its solvates or the crystalline forms of salt of Formula A or its solvates (such as Form A-I, Form B-I, Form B-II, Form B-III, Form C-I, Form C-II, and Form C-III), which are reproducible and easy in operation.

In still another aspect, the present invention provides the pharmaceutical compositions comprising an effective amount of one or more of salt of Formula A or its solvates or the crystalline forms of salt of Formula A or its solvates (such as Form A-I, Form B-I, Form B-II, Form B-III, Form C-I, Form C-II, and Form C-III), and remaining amount of at least one pharmaceutically acceptable carrier.

The present invention further provides a method of treating diseases responsive to inhibition of Syk kinase activity, comprising administering to a subject in need thereof an effective amount of one or more of salt of Formula A or its solvates or the crystalline forms of salt of Formula A or its solvates of the present invention, such as Form A-I, Form B-I, Form B-II, Form B-III, Form C-II, or Form C-III.

The present invention further provides a use of salt of Formula A or its solvates or the crystalline forms of salt of Formula A or its solvates (such as Form A-I, Form B-I, Form B-II, Form B-III, Form C-I, Form C-II, or Form C-III) in the manufacture of a medicament for treating diseases responsive to inhibition of Syk kinase activity, such as autoimmune diseases, inflammatory diseases, and cancer (preferably hematological malignancy), e.g. systemic lupus erythematosus, rheumatoid arthritis, Sjorgen's syndrome, IgA nephropathy, autoimmune hemolytic anemia, idiopathic thrombocytopenic purpura, multiple sclerosis, myasthenia gravis, allergic rhinitis, chronic obstructive pulmonary disease, adult respiratory distress syndrome, asthma, lymphoma (such as B cell lymphoma, T cell lymphoma), leukemia (such as chronic lymphocytic leukemia, acute lymphocytic leukemia, and acute myeloid leukemia), and multiple myeloma.

DEFINITIONS

Figure 1:
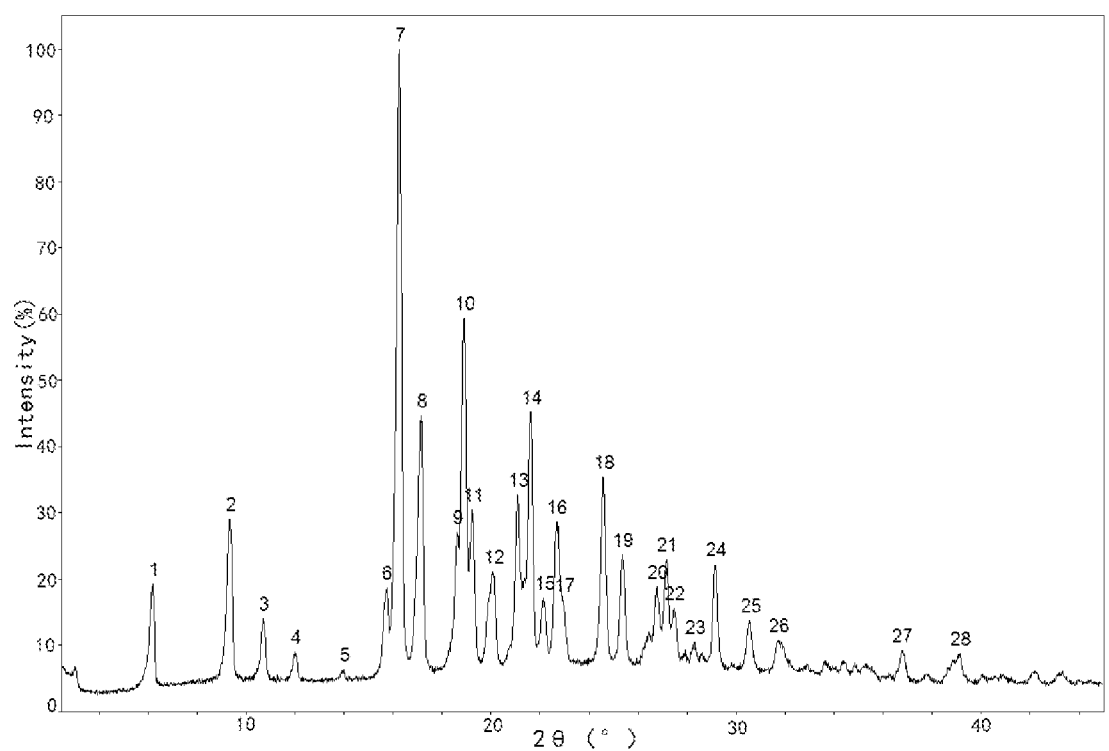
FIG. 1 shows an X-ray powder diffractogram of Form A-I of salt of Formula A, wherein the horizontal axis (X-axis) plots the diffraction angle 2 theta, and the vertical axis (Y-axis) plots the diffraction intensity (%).

Unless indicated otherwise, the following abbreviations or terms as used in the present application (including the specification and the claims) have the meanings as set forth below. It is to be noted that the singular forms and the articles "a", "an" and "the" in the specification and the claims include plural references, unless clearly indicated otherwise.

The term "crystalline forms of the present invention" as used herein refers to the crystalline forms Form A-I, Form B-I, Form B-II, Form B-III, Form C-I, Form C-II, or Form C-III of salt of Formula A or the solvates thereof, or a mixture thereof. "Form", "crystalline form" and "polymorph" may be used interchangeably herein.

The term "salt of Formula A" as used herein refers to a salt having the following chemical structure of Formula. A (also referenced as "Salt A"):

Formula A

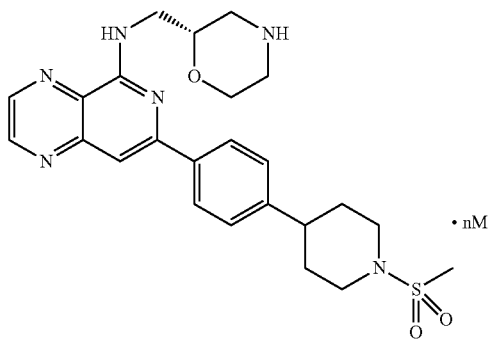

·nM wherein, n is 0.5 or 1;

M is the pharmaceutically acceptable acid molecule.

The term "$C_{1-6}$ alkanol" as used herein refers to a fully saturated straight or branched alkyl alcohol having 1, 2, 3, 4, 5 or 6 carbon atoms. Examples include but not limited to methanol, ethanol, n-propanol, i-propanol, n-butanol, i-butanol, t-butanol, n-pentanol, i-pentanol, n-hexanol, and the like.

The term "haloalkane with less than three carbon atoms" as used herein refers to fully saturated hydrocarbon having 1 or 2 carbon atoms, which is substituted with one or more halogen atoms selected from F, Cl, Br or I. Examples include dichloromethane, trichloromethane, carbon tetrachloride, 1,2-dichloroethane, and the like.

The term "about" as used herein refers to the deviation from a given numerical value of no more than ±10%.

The term "substantially free of other forms" as used herein means that the content of said other forms is less than 50%, preferably less than 40%, preferably less than 30%, preferably less than 20%, preferably less than 10%, preferably less than 5%, preferably less than 1% by weight, based on the total weight of the forms.

The term "solution" as used herein means a mixture of one or more solutes in one or more solvents, for certain use. Solution is intended to encompass homogeneous mixtures as well as heterogeneous mixtures, such as slurries or other suspension mixtures having insoluble (not dissolved) material.

The term "organic solvent" as used herein is broadly intended to mean any appropriate organic solvent for certain use disclosed herein.

The term "dissolution solvent" as used herein refers to any appropriate organic solvent which is capable of dissolving, in whole or in part, the solutes under appropriate conditions, such as an appropriate amount and an appropriate temperature, such as room temperature or an elevated temperature.

The term "anti-dissolution solvent" as used herein refers to any appropriate organic solvent in which the substrate has less solubility than in the dissolution solvent.

The term "pharmaceutically acceptable salts" as used herein includes, but not limited to salts with inorganic acids, such as hydrochlorate, hydrobromate, phosphate, phosphite, sulfite, sulfite, nitrate, and the like; as well as salts with an organic acid, such as malate, maleate, mandelate, fumarate, tartrate, succinate, citrate, aspartate, glutamate, 2-hydroxyl-2-phenylpropionate, gluconate, lactate, camphorsulfonate, methanesulfonate, ethanesulfonate, naphthalenesulfonate, p-Tosylate, 2-hydroxyethylsulfonate, β-hydroxybutyrate, benzoate, salicylate, and alkanoate such as acetate, propionate, stearate, HOOC—(CH2)n-COOH (wherein n is 0-4), and the like.

The term "effective amount" of salt of Formula A and the crystalline forms thereof, solvates and the crystalline forms thereof means an amount which is effective in alleviating, improving, or stopping or delaying the progression of diseases responsive to inhibition of Syk kinase activity, such as autoimmune diseases, inflammatory diseases, and cancer (preferably hematological malignancy) when administered to an individual, which may be a human, animal or the like, wherein the diseases responsive to inhibition of Syk kinase activity, such as autoimmune diseases, inflammatory diseases, and cancer (preferably hematological malignancy) include but not limited to systemic lupus erythematosus, rheumatoid arthritis, Sjorgen's syndrome, IgA nephropathy, autoimmune hemolytic anemia, idiopathic thrombocytopenic purpura, multiple sclerosis, myasthenia gravis, allergic rhinitis, chronic obstructive pulmonary disease, adult respiratory distress syndrome, asthma, lymphoma (such as B cell lymphoma, T cell lymphoma), leukemia (such as chronic lymphocytic leukemia, acute lymphocytic leukemia, and acute myeloid leukemia), and multiple myeloma. "Effective amount" may vary with various factors, such as compound, state of disease to be treated, severity of disease to be treated, age and health status of the individual, administration route and form, judgement of the attending physician or a veterinary practitioner, and so on.

The term "individual" or "subject" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but not limited to, birds, and the like. The term "individual" or "subject" does not denote a particular age or sex.

DETAILED DESCRIPTION OF THE INVENTION

The present invention provides the pharmaceutically acceptable salts of compound (S)-7-(4-(1-(methylsulfonyl)piperidin-4-yl)phenyl)-N-(morpholin-2-ylmethyl)pyrido[3,4-b]pyrazin-5-amine and the crystalline forms thereof, solvates and the crystalline forms thereof.

The crystalline forms of the present invention have good crystallinity, high solubility, and good stability. The crystalline forms of the present invention have good reproducibility and can realize repeatable amplified production; moreover, they are stable in ordinary formulations, so it is convenient for them to be used in the manufacture of formulations and treatment of diseases. In addition, the crystalline forms of the present invention have high purity and less solvent residue, which meet the quality requirements of bulk drug, such as ICH Q3A.

The person of ordinary skill in the art can verify the above advantages of the crystalline forms of the present invention according to the test methods disclosed in the pharmacopoeias and the modification thereof, or the conventional methods in the art.

As described herein, the crystalline forms of the present invention may be identified by one or more solid state analytical methods. For example, the crystalline forms of the present invention may be identified by one or more methods, e.g., X-ray powder diffraction, lattice parameters of a single crystal, Fourier Infrared Spectroscopy, differential scanning calorimetry analytical data, and/or a thermogravimetric curve. Moreover, if the identified or analytical result by one of those methods is consistent with that of the forms of the present invention, it does not mean that the result by any other methods is consistent with that of the forms of the present invention.

As described herein, the new crystalline forms may be identified according to X-ray powder diffraction. However, it is known in the art that the peak intensity and/or measured peaks in the X-ray powder diffractogram may vary with the different experiment condition, e.g., different diffraction test conditions and/or preferred orientations or like. Furthermore, the measured 2θ value may be subjected to an error of about ±0.2 2θ due to different instrument precision. However, it is known that, compared with the positions of peaks, the relative intensity values of the peaks more depend on certain properties of the tested samples, e.g., crystal size in the sample, orientation effect of crystalline and purity of the analysed materials. Therefore, the deviation of the peak intensity at about ±20% or greater may occur. However, despite of experimental errors, instrument errors, preferred orientation and the like, one skilled in the art can obtain sufficient information from the XRPD data provided herein to identify Form A-I and any other crystalline forms of the present invention.

Form A-I

The present invention provides Form A-I of salt of Formula A (wherein, n is 1, M is acetic acid).

In some embodiments, Form A-I of salt f Formula A may be identified according to X-ray powder diffraction. In some embodiments, the X-ray powder diffraction characteristic diffraction angles (2θ) of Form A-I of salt of Formula A include 6.2, 9.4, 16.3, 17.2, and 19.0 degrees, the measured 2θ values each having an error of about ±0.2 degrees (2θ).

In some embodiments, the X-ray powder diffraction characteristic diffraction angles (2θ) of Form A-I of salt of Formula A include 6.2, 9.4, 10.8, 16.3, 17.2, 19.0, 20.1, 21.7, 24.6, and 29.2 degrees, the measured 2θ values each having an error of about ±0.2 degrees (2θ).

In some embodiments, the X-ray powder diffraction characteristic diffraction angles (2θ) of Form A-I of salt of Formula A include 6.2, 9.4, 10.8, 12.1, 15.8, 16.3, 17.2, 19.0, 20.1, 21.7, 22.7, 24.6, 25.4, and 29.2 degrees, the measured 2θ values each having an error of about ±0.2 degrees (2θ).

In some embodiments, the X-ray powder diffraction characteristic diffraction angles (2θ) of Form A-I of salt of Formula A include 6.2, 9.4, 10.8, 12.1, 14.1, 15.8, 16.3, 17.2, 19.0, 19.3, 20.1, 21.1, 21.7, 22.2, 22.7, 24.6, 25.4, and 29.2 degrees, the measured 2θ values each having an error of about ±0.2 degrees (2θ).

In some embodiments, the X-ray powder diffraction characteristic diffraction angles (2θ) of Form A-I of salt of Formula A include 6.2, 9.4, 10.8, 12.1, 14.1, 15.8, 16.3, 17.2, 19.0, 19.3, 20.1, 21.1, 21.7, 22.2, 22.7, 24.6, 25.4, 26.8, 27.2, 27.5, 29.2, 30.6, and 31.8 degrees, the measured 2θ values each having an error of about ±0.2 degrees (2θ).

In some embodiments, Form A-I of salt of Formula A has a diffractogram as shown in FIG. 1. Despite of experimental errors, instrument errors, preferred orientation and the like, one skilled in the art can obtain sufficient information from the XRPD data provided herein to identify Form A-I of salt of Formula A.

Figure 2:
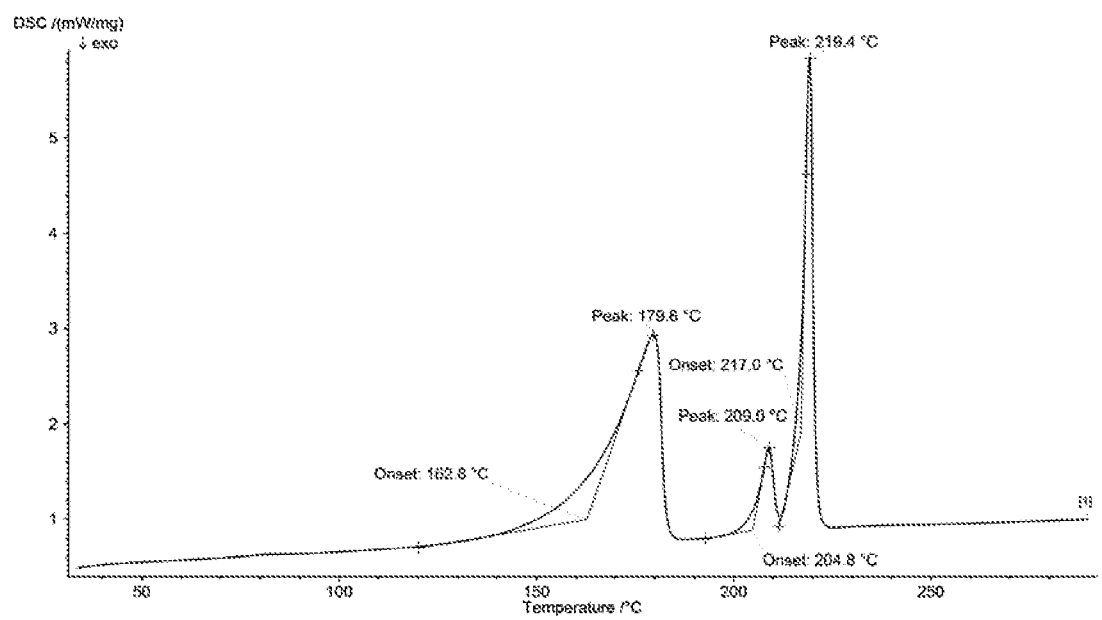
FIG. 2 shows a differential scanning calorimetry (DSC) profile of Form A-I of salt of Formula A, wherein the horizontal axis (X-axis) plots the temperature (° C.), and the vertical axis (Y-axis) plots the heat flow (mW).

In some embodiments, Form A-I of salt of Formula A may be characterized by differential scanning calorimetry (DSC). In some embodiments, Form A-I of salt of Formula A has a DSC curve as shown in FIG. 2. In the DSC profile, the endothermic peaks of Form A-I of salt of Formula A are at about 162.8-1796° C. and 217.0-219.4° C.

Figure 3:
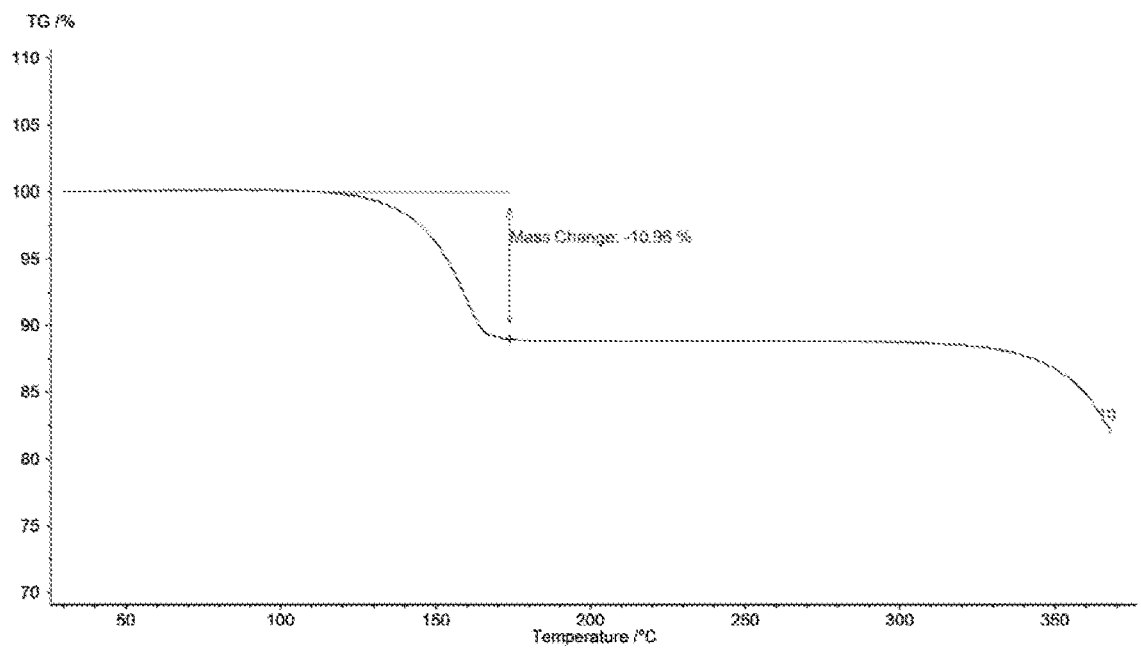
FIG. 3 shows a Thermogravimetric (TG) profile of Form A-I of salt of Formula A, wherein the horizontal axis (X-axis) plots the temperature (° C.), and the vertical axis (Y-axis) plots the weight percentage (%).

In some embodiments, Form A-I of salt of Formula A may be characterized by thermogravimetric analysis (TGA). In some embodiments, Form A-I of salt of Formula A has a TGA curve as shown in FIG. 3, indicating that it has weight loss of about 10.96% between 100-170° C., being the loss of acetic acid when heated, Form A-I is an anhydrous material or a neat crystal.

In some embodiments, Form A-I of salt of Formula A is substantially free of other crystalline forms as described herein. For example, the content by weight of Form A-I of salt of Formula A is at least 99%, at least 95%, at least 90%, or even lower to 80%. Further, the content by weight of Form A-I of salt of Formula A is at least 70%, or at least 60%. Even further, the content by weight of Form A-I of salt of Formula A is at least 50%.

Methods of Preparing Form A-I

Method A

The present invention relates to a method of preparing Form A-I of salt of Formula A, comprising:

(1) reacting the compound (S)-7-(4-(1-(methylsulfonyl) piperidin-4-yl)phenyl)-N-(morpholin-2-ylmethyl)pyrido[3,4-b]pyrazin-5-amine with acetic acid to form a salt, which is stirred in at least one dissolution solvent or a mixed solvent consisting of water miscible organic solvent and water;

(2) isolating to obtain the solid Form A-I of (S)-7-(4-(1-(methylsulfonyl)piperidin-4-yl) phenyl)-N-(morpholin-2-ylmethyl)pyrido[3,4-b]pyrazin-5-amine acetate;

(3) optionally drying the solid obtained in step (2).

In some embodiments, the mole ratio of acetic acid to compound (S)-7-(4-(1-(methylsulfonyl)piperidin-4-yl phenyl)-N-(morpholin-2-ylmethyl)pyrido[3,4-b]pyrazin-5-amine is no less than about 1:1. In some embodiments, the mole ratio is about 1.5:1. In some embodiments, the mole ratio is about 2:1. In some embodiments, the mole ratio is about 3:1. In some embodiments, the mole ratio is about 10:1. In some embodiments, the mole ratio is about 25:1.

In some embodiments, the ratio of the volume (mL) of the dissolution solvent or the mixed solvent to the weight (g) of compound (S)-7-(4-(1-(methylsulfonyl)piperidin-4-yl)phenyl)-N-(morpholin-2-ylmethyl)pyrido[3,4-b]pyrazin-5-amine in step (1) is no less than about 10 mL/g (volume/weight ratio), such as 13 mL/g, 18 mL/g, 23 mL/g, 24 mL/g, 25 mL/g, 31 mL/g, 35 mL/g, 90 mL/g, 100 mL/g.

In some embodiments, said dissolution solvent is selected from $C_{1-6}$ alkanol, tetrahydrofuran, dioxane, haloalkane with less than three carbon atoms, acetone, butanone, and acetonitrile. In some embodiments, said dissolution solvent is selected from methanol, ethanol, i-propanol, t-butanol, dioxane, acetone, and acetonitrile. In some embodiments, said dissolution solvent is selected from ethanol, i-propanol, and dioxane.

In some embodiments, the volume percentage of said water miscible organic solvent in said mixed solvent is less than about 95%.

In some embodiments, said water miscible organic solvent is selected from acetone, $C_{1-6}$ alkanol (such as methanol, ethanol, i-propanol), dioxane, and acetonitrile. In some embodiments, said water miscible organic solvent is selected from acetone, ethanol, and dioxane.

In some embodiments, said water miscible organic solvent and water are mixed in an appropriate ratio. In some embodiments, the volume ratio of the water miscible organic solvent to water ranges from about 15:1 to 3:1, such as ethanol/water (about 11.6:1 in WV), acetone/water (about 11:1 in V/V), dioxane/water (about 8:1 in V/V).

In some embodiments, in step (1), the salt is formed under heating and/or stirring. The heating temperature is not higher than the boiling point of the solvent system, such as about 40-50° C., about 60-70° C., and about 80-85° C.

In some embodiments, in step (1), the formed salt is stirred under cooling, preferably cooling naturally, such as cooling to room temperature or lower temperature, e.g. about 20-25° C., about 5-10° C., and about 0-5° C.

In some embodiments, in step (1), the formed salt is stirred for 1-120 hours, such as at least 1 hour, at least 2 hours, at least 12 hours, at least 17 hours, at least 24 hours, at least 72 hours, at least 120 hours.

In some embodiments, the drying temperature and drying time in step (3) should be appropriate so that the solid is dried sufficiently and the desired crystalline properties are maintained. In some embodiments, the drying temperature is. 55° C. In some embodiments, the drying temperature is 60° C.

Method B

The present invention provides a further method of preparing Form A-I of salt of Formula A, comprising:

(1) adding the compound (S)-7-(4-(1-(methylsulfonyl) piperidin-4-yl)phenyl)-N-(morpholin-2-ylmethyl)pyrido[3,4-b]pyrazin-5-amine and acetic acid into an appropriate amount of at least one dissolution solvent or of a mixed solvent consisting of water miscible organic solvent and water, and reacting to form a salt, thereby obtaining the first solution;

(2) adding at least one anti-dissolution solvent into said first solution to obtain the second solution;

(3) isolating to obtain the solid Form A-I of (S)-7-(4-(1-(methylsulfonyl)piperidin-4-yl) phenyl)-N-(morpholin-2-ylmethyl)pyrido[3,4-b]pyrazin-5-amine acetate;

(4) optionally drying the solid obtained in step (3).

In some embodiments, said dissolution solvent is selected from $C_{1-6}$ alkanol (such as ethanol, i-propanol), and dichloromethane.

In some embodiments, said water miscible organic solvent is selected from $C_{1-6}$ alkanol (such as methanol, ethanol, i-propanol), dioxane, acetone, and acetonitrile. In some embodiments, said water miscible organic solvent is selected from ethanol. The volume percentage of ethanol in said mixed solvent is no less than about 50%, such as 86.4%, 95%.

In some embodiments, said anti-dissolution solvent is selected from acetone, isopropyl ether, and methyl tert-butyl ether.

In some embodiments, the volume ratio of the dissolution solvent or the mixed solvent to the anti-dissolution solvent ranges from about 1:2 to about 30:1, such as 1:2.3, 3.2:1, 4:1, 27.5:1.

In some embodiments, stirring is applied in step (1), and heating may be applied concomitantly. The heating temperature is not higher than the boiling point of the solvent system, such as about 40-50° C., about 60-64° C., and about 80° C.

Form B-I

The present invention provides Form B-I of salt of Formula A (wherein, n is 1, M is p-toluenesulfonic acid).

In some embodiments, Form B-I of salt of Formula A may be identified according to X-ray powder diffraction. In some embodiments, the X-ray powder diffraction characteristic diffraction angles (2θ) of Form B-I of salt of Formula A include 4.9, 5.5, 9.6, 14.4, 16.4, and 19.8 degrees, the measured 2θ values each having an error of about 0.2 degrees (2θ).

In some embodiments, the X-ray powder diffraction characteristic diffraction angles (2θ) of Form B-I of salt of Formula A include 4.9, 5.5, 9.6, 14.4, 15.9, 16.4, 17.3, 18.4, 19.3, and 19.8 degrees, the measured 2θ values each having an error of about ±0.2 degrees (2θ).

In some embodiments, the X-ray powder diffraction characteristic diffraction angles (2θ) of Form B-I of salt of Formula A include 4.9, 5.5, 6.8, 9.6, 10.1, 14.4, 14.8, 15.9, 16.4, 17.3, 18.4, 19.3, 19.8, 22.5, and 23.2 degrees, the measured 2θ values each having an error of about ±0.2 degrees (2θ).

In some embodiments, the X-ray powder diffraction characteristic diffraction angles (2θ) of Form B-I of salt of Formula A include 4.9, 5.5, 6.8, 9.6, 10.1, 14.4, 14.8, 15.9, 16.4, 17.3, 18.4, 19.3, 19.8, 20.7, 21.4, 22.5, 23.2, 25.0, 26.1, 27.0, and 29.0 degrees, the measured 2θ values each having an error of about ±0.2 degrees (2θ).

Figure 4:
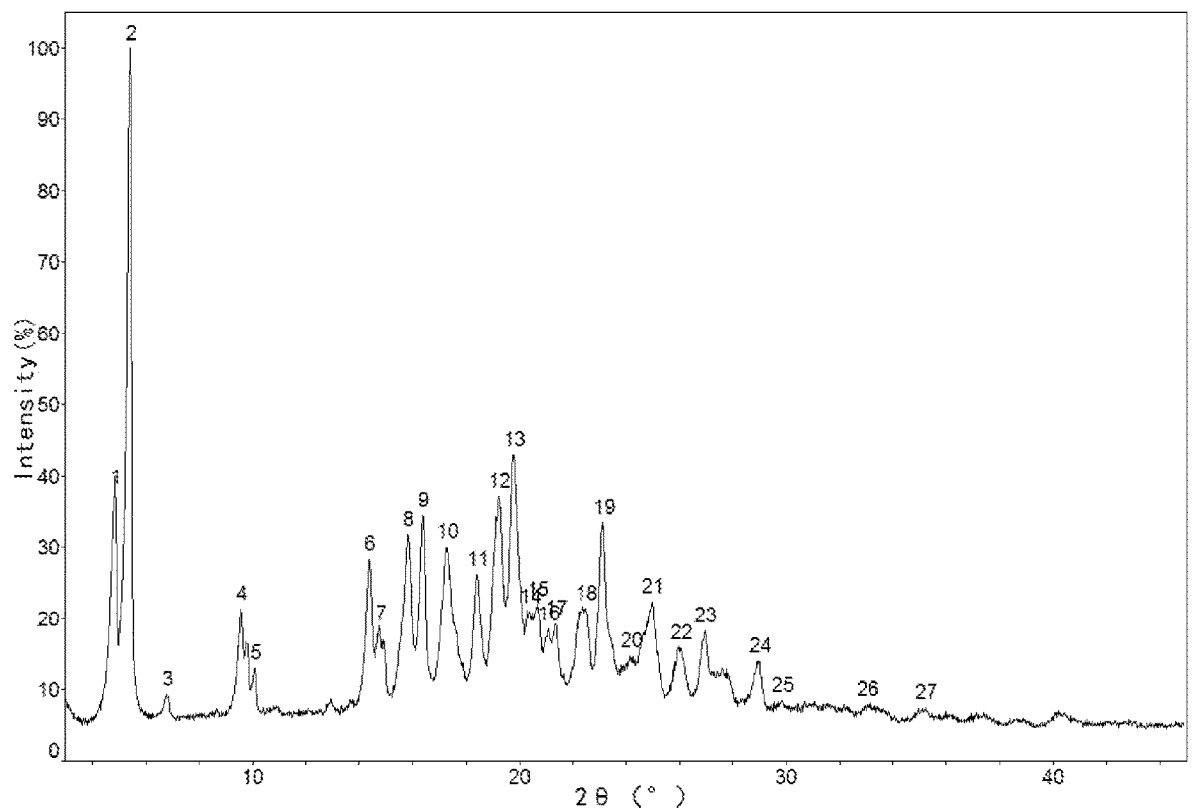
FIG. 4 shows an X-ray powder diffractogram of Form B-I of salt of Formula A, wherein the horizontal axis (X-axis) plots the diffraction angle 2 theta, and the vertical axis (Y-axis) plots the diffraction intensity (%).

In some embodiments, Form B-I of salt of Formula A has a diffractogram as shown in FIG. 4. Despite of experimental errors, instrument errors, preferred orientation and the like, one skilled in the art can obtain sufficient information from the XRPD data provided herein to identify Form B-I of salt of Formula A.

Figure 5:
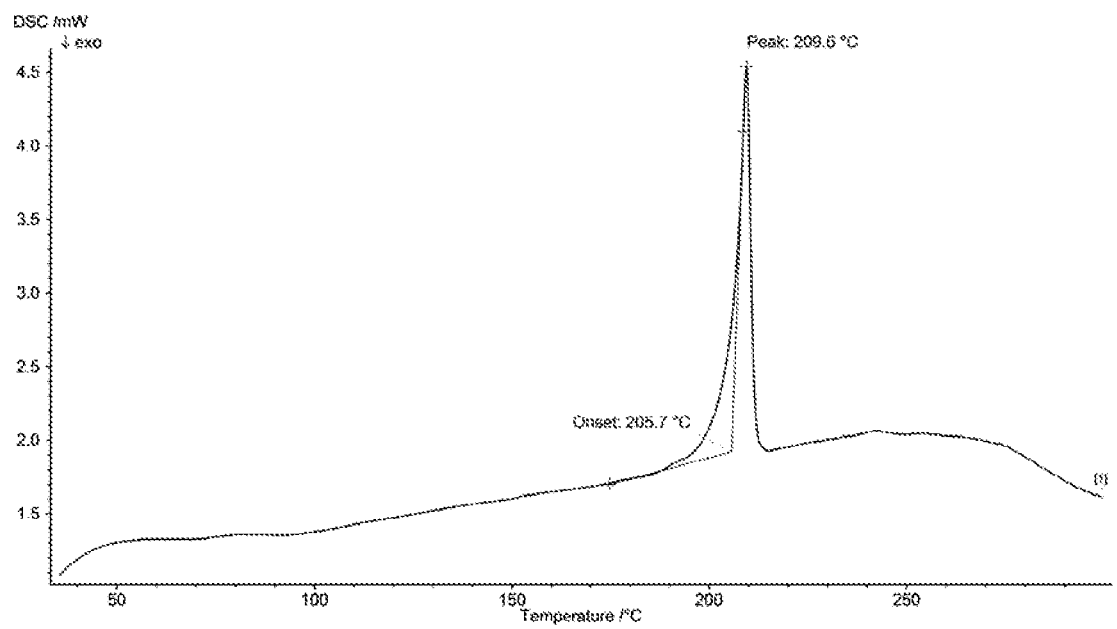
FIG. 5 shows a differential scanning calorimetry (DSC) profile of Form B-I of salt of Formula A, wherein the horizontal axis (X-axis) plots the temperature (° C.), and the vertical axis (Y-axis) plots the heat flow (mW).

In some embodiments, Form B-I of salt of Formula A may be characterized by differential scanning calorimetry (DSC). In some embodiments, Form B-I of salt of Formula A has a DSC curve as shown in FIG. 5. In the DSC profile, the endothermic peak of Form of salt of Formula A is at about 205.7-209.6° C.

Figure 6:
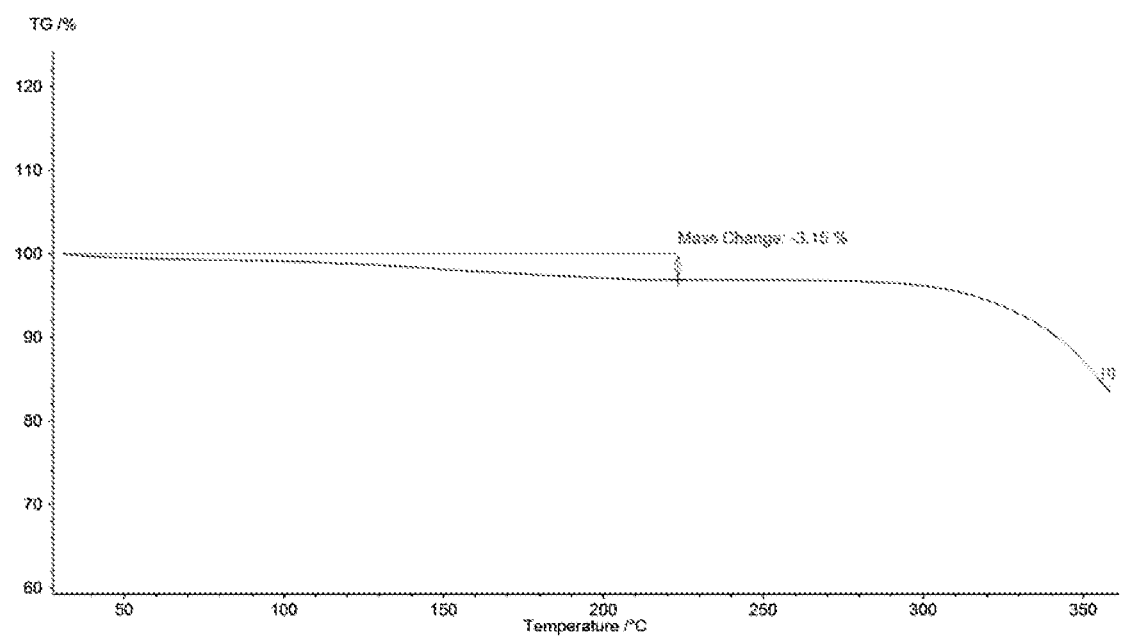
FIG. 6 shows a Thermogravimetric (TG) profile of Form B-I of salt of Formula A, wherein the horizontal axis (X-axis) plots the temperature (° C.), and the vertical axis (Y-axis) plots the weight percentage (%).

In some embodiments, Form B-I of salt of Formula A may be characterized by thermogravimetric analysis (TGA). In some embodiments, Form B-I of salt of Formula A has a TGA curve as shown in FIG. 6, indicating that Form B-I is an anhydrous material or a neat crystal.

In some embodiments, Form of salt of Formula A is substantially free of other crystalline forms as described herein. For example, the content by weight of Form B-I of salt of Formula A is at least 99%, at least 95%, at least 90%, or even lower to 80%. Further, the content by weight of Form B-I of salt of Formula A is at least 70%, or at least 60%. Even further, the content by weight of Form B-I of salt of Formula A is at least 50%.

Methods of Preparing Form B-I.

Method A

The present invention relates to a method of preparing Form B-I of salt of Formula A, comprising:

(1) reacting the compound (S)-7-(4-(1-(methylsulfonyl) piperidin-4-yl)phenyl)-N-(morpholin-2-ylmethyl)pyrido[3,4-b]pyrazin-5-amine with p-toluenesulfonic acid to form a salt, which is stirred in a mixed solvent consisting of water miscible organic solvent and water;

(2) isolating to obtain the solid Form of (S)-7-(4-(1-(methylsulfonyl)piperidin-4-yl) phenyl)-N-(morpholin-2-ylmethyl)pyrido[3,4-b]pyrazin-5-amine p-Tosylate;

(3) optionally drying the solid obtained in step (2).

In some embodiments, the mole ratio of p-toluenesulfonic acid to compound (S)-7-(4-(1-(methylsulfonyl)piperidin-4-yl)phenyl)-N-(morpholin-2-ylmethyl)pyrido[3,4-b]pyrazin-5-amine is no less than about 1:1. In some embodiments, the mole ratio is about 1.1:1.

In some embodiments, the ratio of the volume (mL) of the mixed solvent to the weight (g) of compound (S)-7-(4-(1-(methylsulfonyl)piperidin-4-yl)phenyl)-N-(morpholin-2-ylmethyl) pyrido[3,4-b]pyrazin-5-amine in step (1) is no less than about 10 mL/g (volume/weight ratio), such as 25 mL/g, 32 mL/g, 33.5 mL/g, 37 mL/g, 42 mL/g, 52 mL/g.

In some embodiments, the volume percentage of said water miscible organic solvent in said mixed solvent is less than about 96%.

In some embodiments, said water miscible organic solvent is selected from $C_{1-6}$ alkanol (such as ethanol, i-propanol), and acetone. In some embodiments, said water miscible organic solvent is selected from ethanol and i-propanol.

In some embodiments, said water miscible organic solvent and water are mixed in an appropriate ratio. In some embodiments, the volume ratio of the water miscible organic solvent to water ranges from about 22:1 to 4:1, such as ethanol/water (about 4.3:1, about 7.7:1, or about 13:1 in V/V), i-propanol/water (about 4.3:1, or about 17.4:1 in V/V), acetone/water (about 22:1 in V/V).

In some embodiments, in step (1), the salt is formed under heating and/or stirring. The heating temperature is not higher than the boiling point of the solvent system, such as about 50-60° C., and about 80-90° C.

In some embodiments, in step (1), the formed salt is stirred under cooling, preferably cooling naturally, such as cooling to room temperature or lower temperature, e.g. about 15-20° C.

In some embodiments, in step (1), the formed salt is stirred for 1-120 hours, such as at least 3 hours, at least 16 hours, at least 72 hours.

In some embodiments, the drying temperature and drying time in step (3) should be appropriate so that the solid is dried sufficiently and the desired crystalline properties are maintained. In some embodiments, the drying temperature is room temperature. In some embodiments, the drying temperature is 60° C.

Method B

The present invention provides a further method of preparing Form B-I of salt of Formula A, comprising:

stirring Form B-II of salt of Formula A in about 95% ethanol at the temperature of about 10-30° C., such as at room temperature to obtain Form B-I.

In some embodiments, the stirring time is 4 days.

Form B-II

The present invention provides Form B-II of salt of Formula A (wherein, n is 1, M is p-toluenesulfonic acid).

In some embodiments, Form B-II of salt of Formula A may be identified according to X-ray powder diffraction. In some embodiments, the X-ray powder diffraction characteristic diffraction angles (2θ) of Form B-II of salt of Formula A include 5.1, 6.0, 10.2, 17.1, and 19.1 degrees, the measured 2θ values each having an error of about ±0.2 degrees (2θ).

In some embodiments, the X-ray powder diffraction characteristic diffraction angles (2θ) of Form B-II of salt of Formula A include 5.1, 6.0, 9.5, 10.2, 14.8, 15.8, 17.1, 19.1, and 22.4 degrees, the measured 2θ values each having an error of about ±0.2 degrees (2θ).

In some embodiments, the X-ray powder diffraction characteristic diffraction angles (2θ) of Form B-II of salt of Formula A include 5.1, 6.0, 9.5, 10.2, 14.3, 14.8, 15.8, 17.1, 19.1, 20.2, 20.8, 22.4, and 26.0 degrees, the measured 2θ values each having an error of about 0.2 degrees (2θ).

In some embodiments, the X-ray powder diffraction characteristic diffraction angles (2θ) of Form B-II of salt of Formula A include 5.1, 6.0, 9.5, 10.2, 14.3, 14.8, 15.3, 15.8, 17.1, 17.9, 19.1, 19.7, 20.2, 20.8, 22.4, 23.4, 26.0, and 27.2 degrees, the measured 2θ values each having an error of about ±0.2 degrees (2θ).

Figure 7:
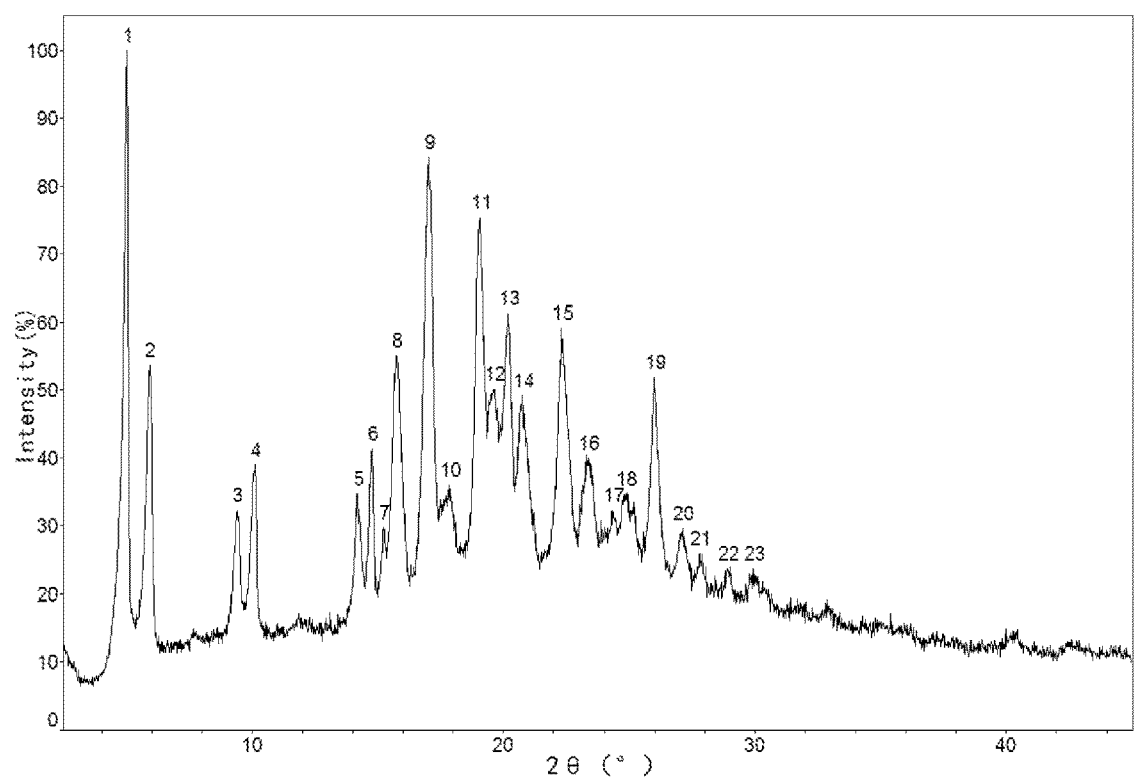
FIG. 7 shows an X-ray powder diffractogram of Form B-II of salt of Formula A, wherein the horizontal axis (X-axis) plots the diffraction angle 2 theta, and the vertical axis (Y-axis) plots the diffraction intensity (%).

In some embodiments, Form B-II of salt of Formula A has a diffractogram as shown in FIG. 7. Despite of experimental errors, instrument errors, preferred orientation and the like, one skilled in the art can obtain sufficient information from the XRPD data provided herein to identify Form B-II of salt of Formula A.

Figure 8:
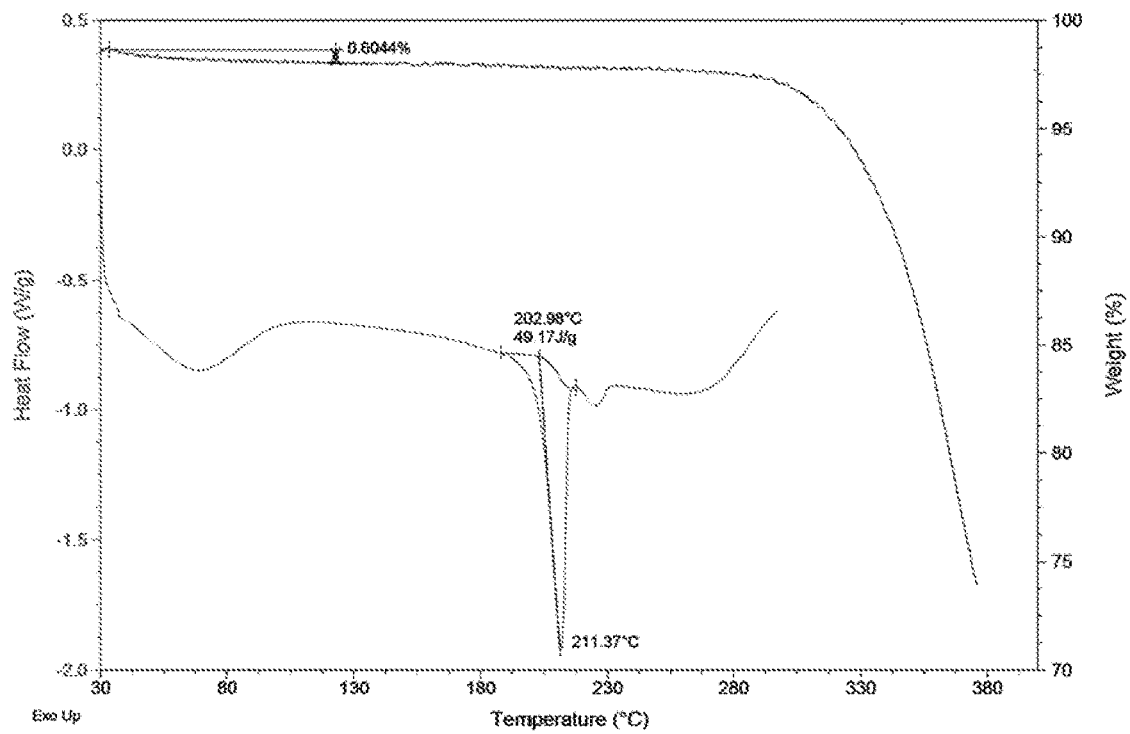
FIG. 8 shows a differential scanning calorimetry (DSC) profile and a Thermogravimetric (TG) profile of Form B-II of salt of Formula A, wherein the horizontal axis (X-axis) plots the temperature (° C.), and the vertical axis (Y-axis) plots the heat flow (mW) and the weight percentage (%).

In some embodiments, Form B-II of salt of Formula A may be characterized by differential scanning calorimetry (DSC). In some embodiments, Form B-II of salt of Formula A has a DSC curve as shown in FIG. 8. In the DSC profile, the endothermic peak of Form B-II of salt of Formula A is at about 203.0-211.4° C.

In some embodiments, Form B-II of salt of Formula A may be characterized by thermogravimetric analysis (TGA). In some embodiments, Form B-II of salt of Formula A has a TGA curve as shown in FIG. 8, indicating that Form B-II is an anhydrous material or a neat crystal.

In some embodiments, Form B-II of salt of Formula A is substantially free of other crystalline forms as described herein. For example, the content by weight of Form B-II of salt of Formula A is at least 99%, at least 95%, at least 90%, or even lower to 80%. Further, the content by weight of Form B-II of salt of Formula A is at least 70%, or at least 60%. Even further, the content by weight of Form B-II of salt of Formula A is at least 50%.

Methods of Preparing Form B-II

The present invention relates to the method of preparing Form B-II of salt of Formula A, comprising:

(1) reacting the compound (S)-7-(4-(1-(methylsulfonyl)piperidin-4-yl)phenyl)-N-(morpholin-2-ylmethyl)pyrido[3,4-b]pyrazin-5-amine with p-toluenesulfonic acid to form a salt, which is stirred in a mixed solvent consisting of methanol and water;

(2) isolating to obtain the solid Form B-II of (S)-7-(4-(1-(methylsulfonyl)piperidin-4-yl) phenyl)-N-(morpholin-2-ylmethyl)pyrido[3,4-b]pyrazin-5-amine p-Tosylate;

(3) optionally drying the solid obtained in step (2).

In some embodiments, the mole ratio of p-toluenesulfonic acid to compound (S)-7-(4-(1-(methylsulfonyl)piperidin-4-yl)phenyl)-N-(morpholin-2-ylmethyl)pyrido[3,4-b]pyrazin-5-amine is no less than about 1:1. In some embodiments, the mole ratio is about 1.1:1.

In some embodiments, the ratio of the volume (mL) of the mixed solvent to the weight (g) of compound (S)-7-(4-(1-(methylsulfonyl)piperidin-4-yl)phenyl)-N-(morpholin-2-ylmethyl) pyrido[3,4-b]pyrazin-5-amine in step (1) is no less than about 10 mL/g (volume/weight ratio), such as about 32 mL/g.

In some embodiments, the volume ratio of methanol to water in step (1) is about 13:1.

In some embodiments, in step (1), the salt is formed under heating and/or stirring. The heating temperature is not higher than the boiling point of the solvent system.

In some embodiments, in step (1), the formed salt is stirred under cooling, preferably cooling naturally, such as cooling to room temperature.

In some embodiments, in step (1), the formed salt is stirred for 1-120 hours, such as at least 72 hours.

Hydrate (Form B-III)

The present invention further provides hydrate of salt of Formula A (wherein, n is 1, M is p-toluenesulfonic acid).

In some embodiments, hydrate of salt of Formula A (wherein, n is 1, M is p-toluenesulfonic acid) is hemihydrate.

In some embodiments, hemihydrate of salt of Formula A (wherein, n is 1, M is p-toluenesulfonic acid) is Form B-III.

In some embodiments, Form B-III of hemihydrate of salt of Formula A may be characterized by X-ray powder diffraction. The X-ray powder diffraction characteristic diffraction angles (2θ) of Form B-III include 5.3, 5.9, 10.7, 13.6, and 15.6 degrees, the measured 2θ values each having an error of about ±0.2 degrees (2θ).

In some embodiments, the X-ray powder diffraction characteristic diffraction angles (2θ) of Form B-III of hemihydrate of salt of Formula A include 5.3, 5.9, 9.9, 10.7, 11.8, 13.6, 14.9, 15.6, and 17.6 degrees, the measured 2θ values each having an error of about ±0.2 degrees (2θ).

In some embodiments, the X-ray powder diffraction characteristic diffraction angles (2θ) of Form B-III of hemihydrate of salt of Formula A include 5.3, 5.9, 9.9, 10.7, 11.8, 13.6, 14.9, 15.6, 16.0, 17.6, 20.0, and 22.8 degrees, the measured 2θ values each having an error of about ±0.2 degrees (2θ).

In some embodiments, the X-ray powder diffraction characteristic diffraction angles (2θ) of form B-III of hemihydrate of salt of Formula A include 5.3, 5.9, 9.9, 10.7, 11.8, 13.6, 14.9, 15.6, 16.0, 17.6, 18.9, 20.0, 21.6, 22.8, 25.0, and 27.0 degrees, the measured 2θ values each having an error of about 0.2 degrees (2θ).

Figure 9:
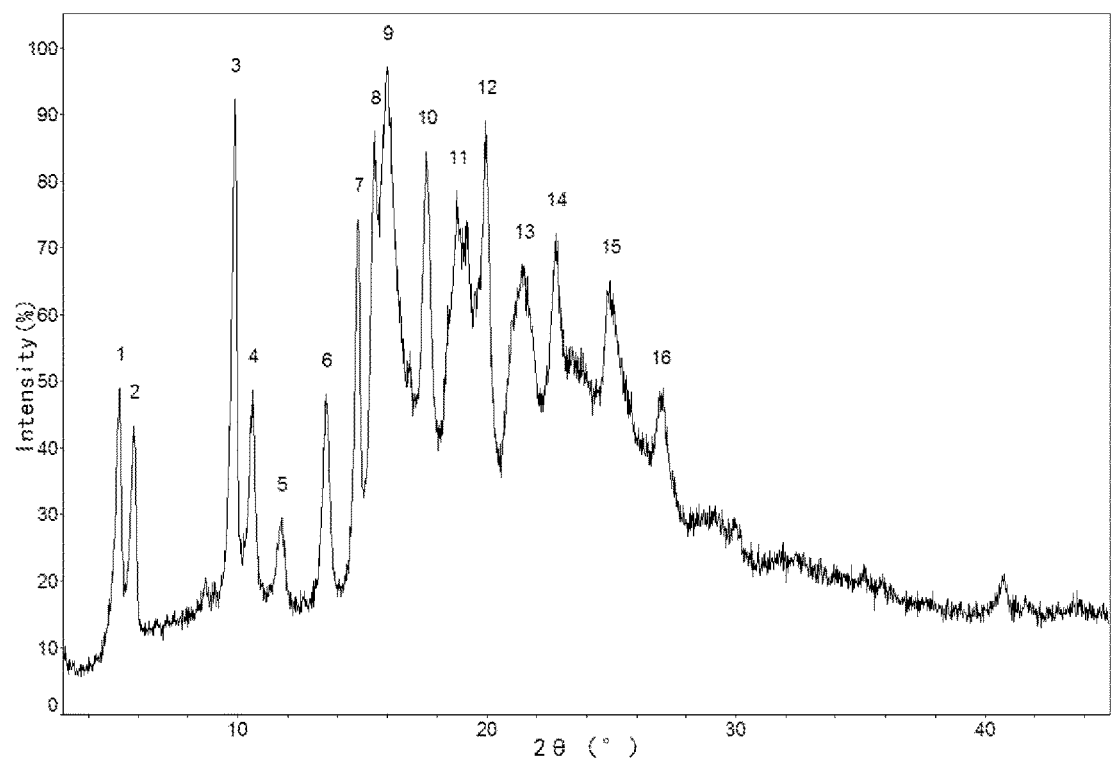
FIG. 9 shows an X-ray powder diffractogram of Form B-III of hemihydrate of salt of Formula A, wherein the horizontal axis (X-axis) plots the diffraction angle 2 theta, and the vertical axis (Y-axis) plots the diffraction intensity (%).

In some embodiments, Form B-III of hemihydrate of salt of Formula A has a diffractogram as shown in FIG. 9. Despite of experimental errors, instrument errors, preferred orientation and the like, one skilled in the art can obtain sufficient information from the XRPD data provided herein to identify Form B-III of hemihydrate of salt of Formula A.

Figure 10:
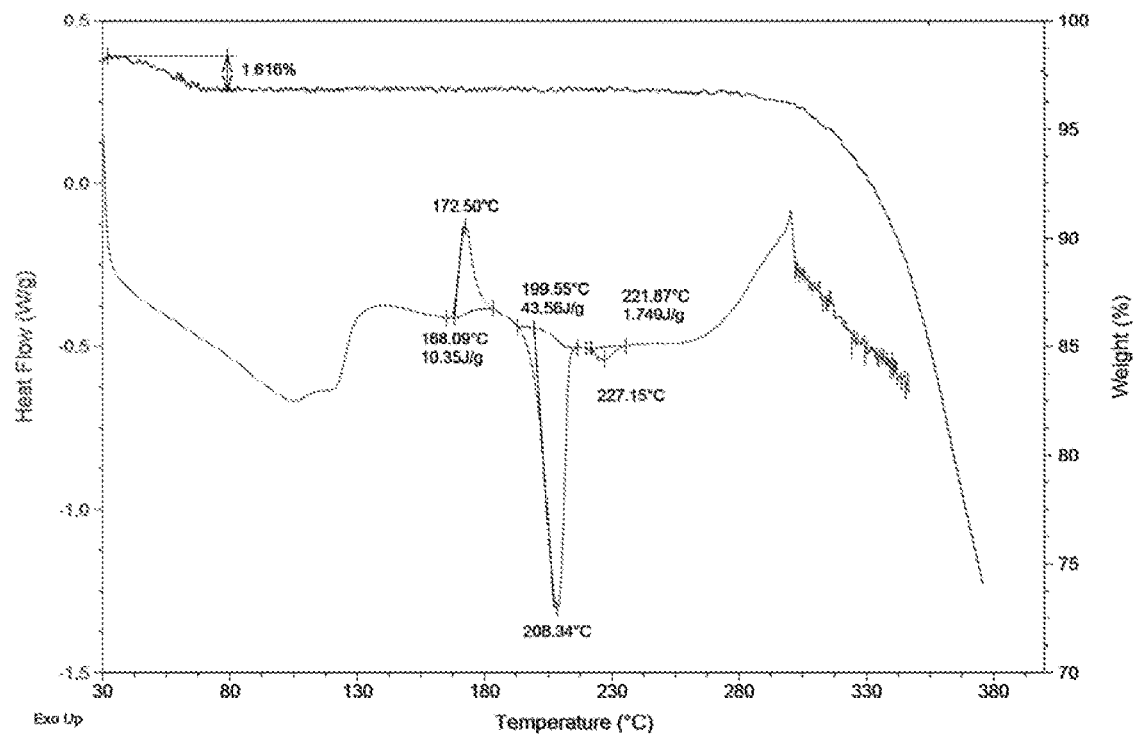
FIG. 10 shows a differential scanning calorimetry (DSC) profile and a Thermogravimetric (TG) profile of Form B-III of hemihydrate of salt of Formula A, wherein the horizontal axis (X-axis) plots the temperature (° C.), and the vertical axis (Y-axis) plots the heat flow (mW) and the weight percentage (%).

In some embodiments, Form B-III of hemihydrate of salt of Formula A may be characterized by differential scanning calorimetry (DSC). In some embodiments, Form B-III of hemihydrate of salt of Formula A has a DSC curve as shown in FIG. 10. In the DSC profile, Form B-III of hemihydrate of salt of Formula A has an exothermic peak at about 168.1-172.5° C., and an obvious endothermic peak at about 199.6-208.3° C.

In some embodiments, Form B-III of hemihydrate of salt of Formula A may be characterized by thermogravimetric analysis (TGA). In some embodiments, Form B-III of hemihydrate of salt of Formula A has a TGA curve as shown in FIG. 10, indicating that Form B-III is a hemihydrate.

In some embodiments, Form B-III of hemihydrate of salt of Formula A is substantially free of other crystalline forms as described herein. For example, the content by weight of Form B-III of hemihydrate of salt of Formula A is at least 99%, at least 95%, at least 90%, or even lower to 80%. Further, the content by weight of Form B-III of hemihydrate of salt of Formula A is at least 70%, or at least 60%. Even further, the content by weight of Form B-III of hemihydrate of salt of Formula A is at least 50%.

Methods of Preparing Form B-III
Method A

The present invention relates to the method of preparing Form B-III of hydrate of salt of Formula A, comprising:

(1) reacting the compound (S)-7-(4-(1-(methylsulfonyl)piperidin-4-yl)phenyl)-N-(morpholin-2-ylmethyl)pyrido[3,4-b]pyrazin-5-amine with p-toluenesulfonic acid to form a salt, which is stirred in water;

(2) isolating to obtain the solid Form B-III of (S)-7-(4-(1-(methylsulfonyl)piperidin-4-yl) phenyl)-N-(morpholin-2-ylmethyl)pyrido[3,4-b]pyrazin-5-amine p-Tosylate;

(3) optionally drying the solid obtained in step (2).

In some embodiments, the mole ratio of p-toluenesulfonic acid to compound (S)-7-(4-(1-(methylsulfonyl)piperidin-4-yl)phenyl)-N-(morpholin-2-ylmethyl)pyrido[3,4-b]pyrazin-5-amine is no less than about 1:1. In some embodiments, the mole ratio is about 1.1:1.

In some embodiments, the ratio of the volume (mL) of water to the weight (g) of compound (S)-7-(4-(1-(methylsulfonyl)piperidin-4-yl)phenyl)-N-(morpholin-2-ylmethyl)pyrido[3,4-b]pyrazin-5-amine in step (1) is about 54 mL/g (volume/weight ratio).

In some embodiments, in step (1), the salt is formed under heating and/or stirring, and the heating temperature should be appropriate, such as about 80-85° C.

In some embodiments, in step (1), the formed salt is stirred under cooling, preferably cooling naturally, such as cooling to room temperature.

Method B

The present invention provides a further method of preparing Form B-III of hydrate of salt of Formula A, comprising:

stirring Form B-I of salt of Formula A in water at the temperature of about 10-30° C., such as at room temperature, collecting the solid by filtration, and optionally drying to obtain Form B-III.

In some embodiments, the stirring time is 4 days.

In some embodiments, the drying is drying under vacuum. In some embodiments, the drying temperature and drying time should be appropriate so that the solid is dried sufficiently and the desired crystalline properties are maintained. In some embodiments, the drying temperature is 60° C. In some embodiments, the drying time is 2 hours.

Form C-I

The present invention provides Form C-I of salt of Formula A (wherein, n is 1, M is malic acid).

In some embodiments, Form C-I of salt of Formula A may be identified according to X-ray powder diffraction. In some embodiments, the X-ray powder diffraction characteristic diffraction angles (2θ) of Form C-I of salt of Formula A include 8.6, 14.3, 15.5, 19.5, and 22.2 degrees, the measured 2θ values each having an error of about ±0.2 degrees (2θ).

In some embodiments, the X-ray powder diffraction characteristic diffraction angles (2θ) of Form C-I of salt of Formula A include 8.6, 10.8, 14.3, 15.5, 16.4, 17.7, 18.4, 19.5, 22.2, and 23.8 degrees, the measured 2θ values each having an error of about ±0.2 degrees (2θ).

In some embodiments, the X-ray powder diffraction characteristic diffraction angles (2θ) of Form C-I of salt of Formula A include 8.6, 10.8, 14.3, 15.5, 16.4, 17.2, 17.7, 18.4, 19.5, 20.9, 22.2, 22.6, 23.8, 29.2, 29.8, and 30.7 degrees, the measured 2θ values each having an error of about ±0.2 degrees (2θ).

In some embodiments, the X-ray powder diffraction characteristic diffraction angles (2θ) of Form C-I of salt of Formula A include 8.6, 10.8, 11.8, 13.5, 14.3, 15.5, 16.4, 17.2, 17.7, 18.1, 18.4, 19.5, 20.9, 22.2, 22.6, 23.8, 25.8, 26.7, 27.8, 29.2, 29.8, and 30.7 degrees, the measured 2θ values each having an error of about ±0.2 degrees (2θ).

Figure 11:
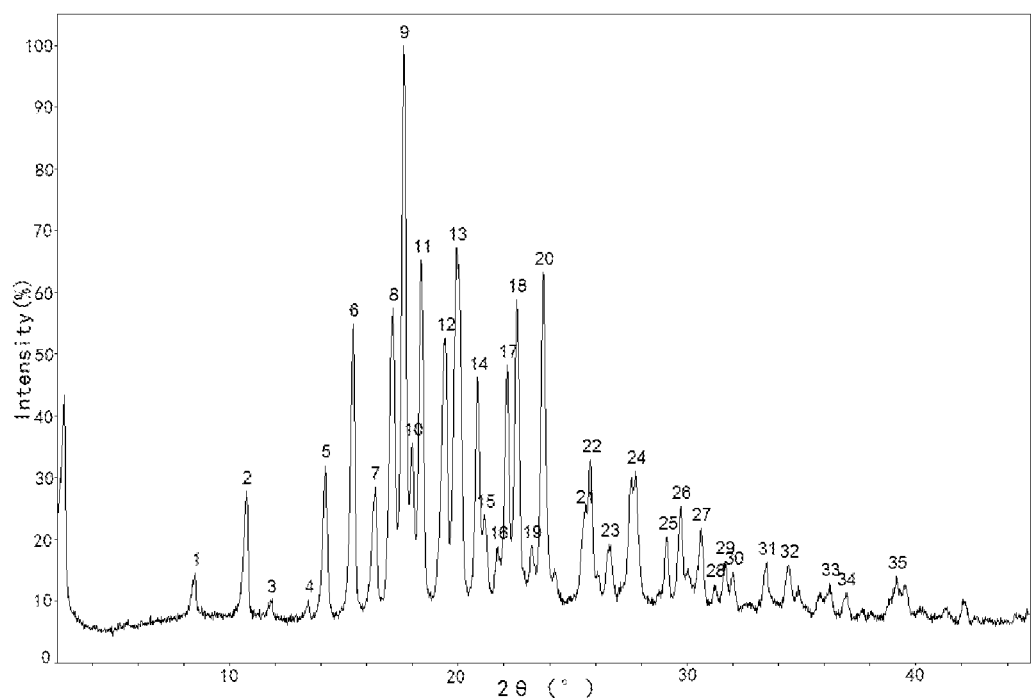
FIG. 11 shows an X-ray powder diffractogram of Form C-I of salt of Formula A, wherein the horizontal axis (X-axis) plots the diffraction angle 2 theta, and the vertical axis (Y-axis) plots the diffraction intensity (%).

In some embodiments, Form C-I of salt of Formula A has a diffractogram as shown in FIG. 11. Despite of experimental errors, instrument errors, preferred orientation and the like, one skilled in the art can obtain sufficient information from the XRPD data provided herein to identify Form C-I of salt of Formula A.

Figure 12:
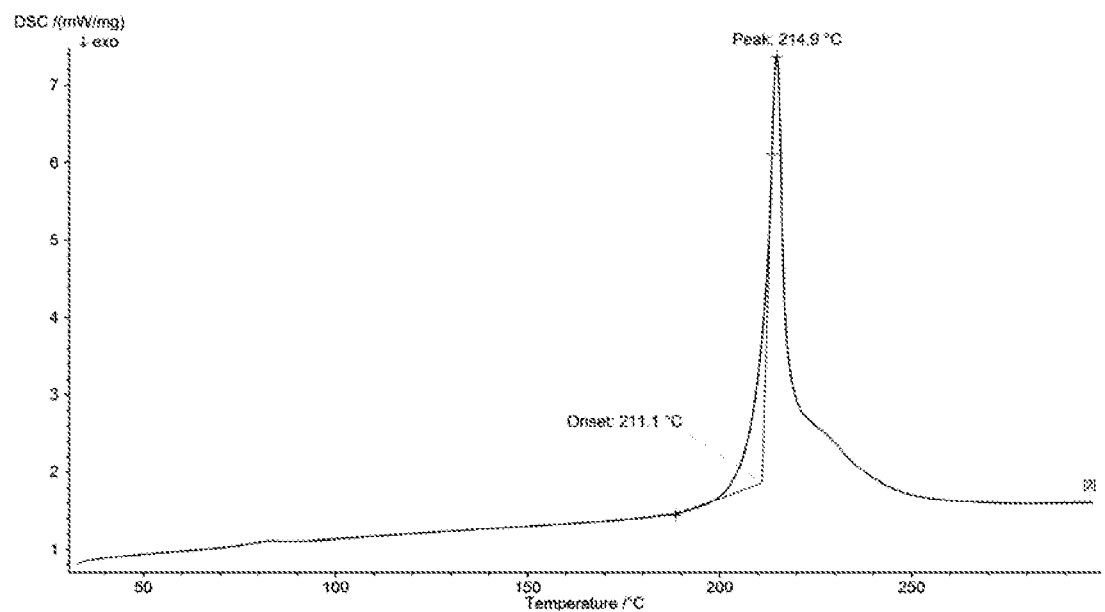
FIG. 12 shows a differential scanning calorimetry (DSC) profile of Form C-I of salt of Formula A, wherein the horizontal axis (X-axis) plots the temperature (° C.), and the vertical axis (Y-axis) plots the heat flow (mW).

In some embodiments, Form C-I of salt of Formula A may be characterized by differential scanning calorimetry (DSC). In some embodiments, Form C-I of salt of Formula A has a DSC curve as shown in FIG. 12. In the DSC profile, the endothermic peak of Form C-I of salt of Formula A is at about 211.1-214.9° C.

Figure 13:
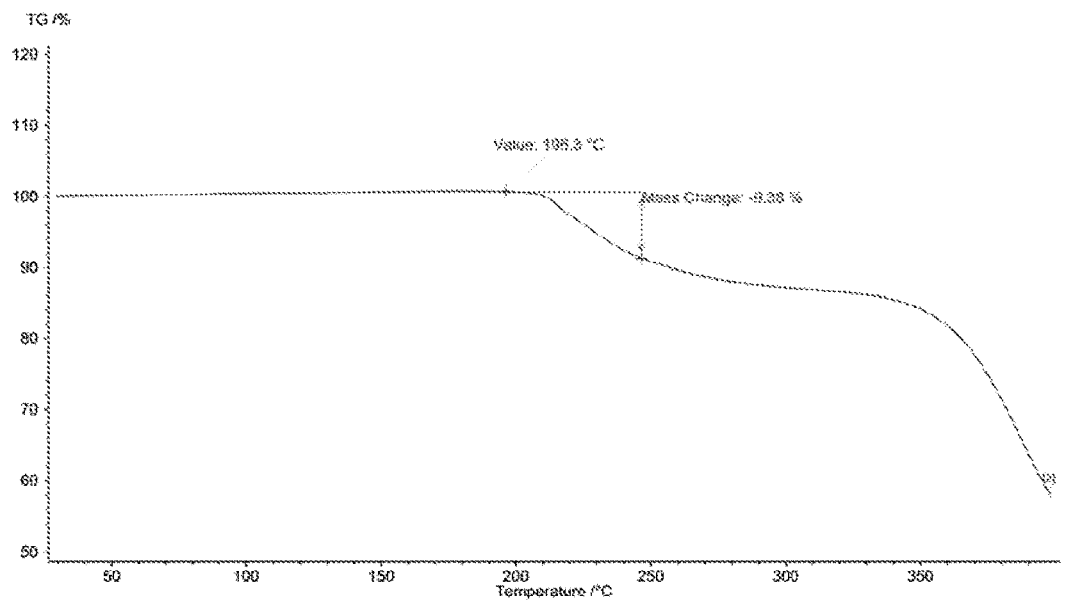
FIG. 13 shows a Thermogravimetric (TG) profile of Form C-I of salt of Formula A, wherein the horizontal axis (X-axis) plots the temperature (° C.), and the vertical axis (Y-axis) plots the weight percentage (%).

In some embodiments, Form C-I of salt of Formula A may be characterized by thermogravimetric analysis (TGA). In some embodiments, Form C-I of salt of Formula A has a TGA curve as shown in FIG. 13, indicating that Form C-I is an anhydrous material or a neat crystal.

In some embodiments, Form C-I of salt of Formula A is substantially free of other crystalline forms as described herein. For example, the content by weight of Form C-I of salt of Formula A is at least 99%, at least 95%, at least 90%, or even lower to 80%. Further, the content by weight of Form C-I of salt of Formula A is at least 70%, or at least 60%. Even further, the content by weight of Form C-I of salt of Formula A is at least 50%.

Methods of Preparing Form C-I

The present invention relates to the method of preparing Form C-I of salt of Formula A, comprising:

(1) reacting the compound (S)-7-(4-(1-(methylsulfonyl)piperidin-4-yl)phenyl)-N-(morpholin-2-ylmethyl)pyrido[3,4-b]pyrazin-5-amine with malic acid to form a salt, which is stirred in at least one dissolution solvent or a mixed solvent consisting of water miscible organic solvent and water;

(2) isolating to obtain the solid Form C-I of (S)-7-(4-(1-(methylsulfonyl)piperidin-4-yl) phenyl)-N-(morpholin-2-ylmethyl)pyrido[3,4-b]pyrazin-5-amine malate; (3) optionally drying the solid obtained in step (2).

In some embodiments, the mole ratio of malic acid to compound (S)-7-(4-(1-(methylsulfonyl)piperidin-4-yl)phenyl)-N-(morpholin-2-ylmethyl)pyrido[3,4-b]pyrazin-5-amine is no less than about 1:1. In some embodiments, the mole ratio is about 1.1:1. In some embodiments, the mole ratio is about 1.5:1.

In some embodiments, the ratio of the volume (mL) of the dissolution solvent or the mixed solvent to the weight (g) of compound (S)-7-(4-(1-(methylsulfonyl)piperidin-4-yl)phenyl)-N-(morpholin-2-ylmethyl)pyrido[3,4-b]pyrazin-5-amine in step (1) is no less than about 30 mL/g (volume/weight ratio), such as 38 mL/g, 53 mL/g, 67 mL/g, 86 mL/g, 135 mL/g.

In some embodiments, said dissolution solvent is selected from $C_{1-6}$ alkanol (such as methanol, ethanol, i-propanol), and tetrahydrofuran. In some embodiments, said dissolution solvent is selected from ethanol.

In some embodiments, said water miscible organic solvent is selected from $C_{1-6}$ alkanol (such as methanol, ethanol, i-propanol), and tetrahydrofuran.

In some embodiments, said water miscible organic solvent and water are mixed in an appropriate ratio. In some embodiments, the volume ratio of the water miscible organic solvent to water ranges from about 12:1 to 1:1, such as ethanol/water (about 1.5:1 in V/V), methanol/water (about 1.5:1 in V/V), i-propanol/water (about 1.4:1 in V/V), tetrahydrofuran/water (about 12:1 in V/V).

In some embodiments, in step (1), the salt is formed under heating and/or stirring. The heating temperature is not higher than the boiling point of the solvent system, such as about 40-50° C., about 60-70° C., and about 75-85° C.

In some embodiments, in step (1), the formed salt is stirred under cooling, preferably cooling naturally, such as cooling to room temperature or lower temperature, e.g. about 15-20° C.

In some embodiments, in step (1), the formed salt is stirred for 1-120 hours, such as at least 12 hours, at least 14 hours, at least 20 hours, at least 72 hours.

In some embodiments, the drying temperature and drying time in step (3) should be appropriate so that the solid is dried sufficiently and the desired crystalline properties are maintained. In some embodiments, the drying temperature is 60° C.

Hydrate (Form C-II)

The present invention further provides hydrate of salt of Formula A (wherein, n is 0.5, M is malic acid).

In some embodiments, hydrate of salt of Formula A (wherein, n is 0.5, M is malic acid) contains 0.75 molecule of water.

In some embodiments, hydrate containing 0.75 molecule of water of salt of Formula A (wherein, n is 0.5, M is malic acid) is Form C-II.

In some embodiments, Form of hydrate of salt of Formula A may be characterized through X-ray powder diffraction. The X-ray powder diffraction characteristic diffraction angles (2θ) of Form C-II include 11.3, 11.6, 17.0, 20.0, 21.6, and 23.1 degrees, the measured 2θ values each having an error of about ±0.2 degrees (2θ).

In some embodiments, the X-ray powder diffraction characteristic diffraction angles (2θ) of Form C-II of hydrate of salt of Formula A include 5.3, 9.5, 10.0, 11.3, 11.6, 17.0, 20.0, 21.6, 23.1, 26.9, and 28.3 degrees, the measured 2θ values each having an error of about 0.2 degrees (2θ).

In some embodiments, the X-ray powder diffraction characteristic diffraction angles (2θ) of Form C-II of hydrate of salt of Formula A include 5.3, 9.5, 10.0, 10.6, 11.3, 11.6, 12.4, 12.8, 17.0, 20.0, 21.6, 23.1, 24.9, 26.4, 26.9, and 28.3 degrees, the measured 2θ values each having an error of about ±0.2 degrees (2θ).

In some embodiments, the X-ray powder diffraction characteristic diffraction angles (2θ) of Form C-II of hydrate of salt of Formula A include 5.3, 9.5, 10.0, 10.6, 11.3, 11.6, 12.4, 12.8, 13.6, 15.9, 17.0, 18.4, 20.0, 20.9, 21.6, 23.1, 24.9, 26.4, 26.9, and 28.3 degrees, the measured 2θ values each having an error of about ±0.2 degrees (2θ).

Figure 14:
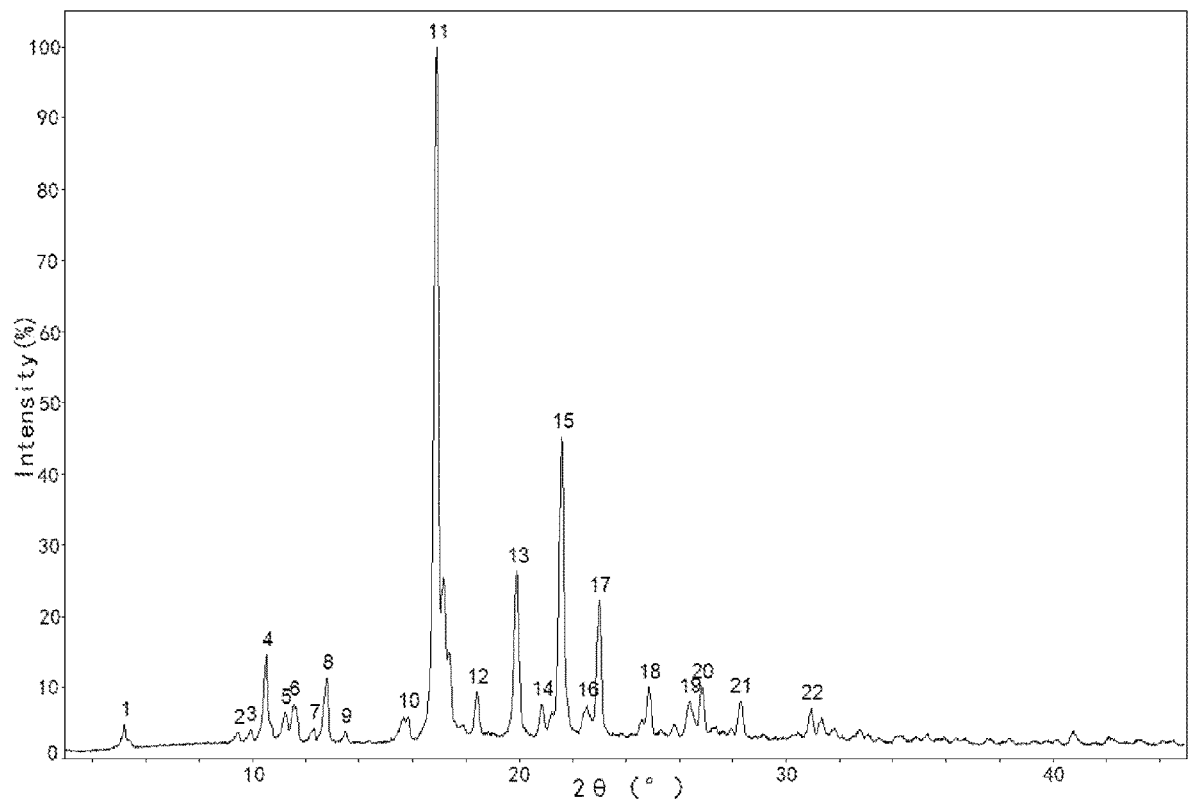
FIG. 14 shows an X-ray powder diffractogram of Form C-II of hydrate of salt of Formula A, wherein the horizontal axis (X-axis) plots the diffraction angle 2 theta, and the vertical axis (Y-axis) plots the diffraction intensity (%).

In some embodiments, Form C-II of hydrate of salt of Formula A has a diffractogram as shown in FIG. 14. Despite of experimental errors, instrument errors, preferred orientation and the like, one skilled in the art can obtain sufficient information from the XRPD data provided herein to identify Form of hydrate of salt of Formula A.

Figure 15:
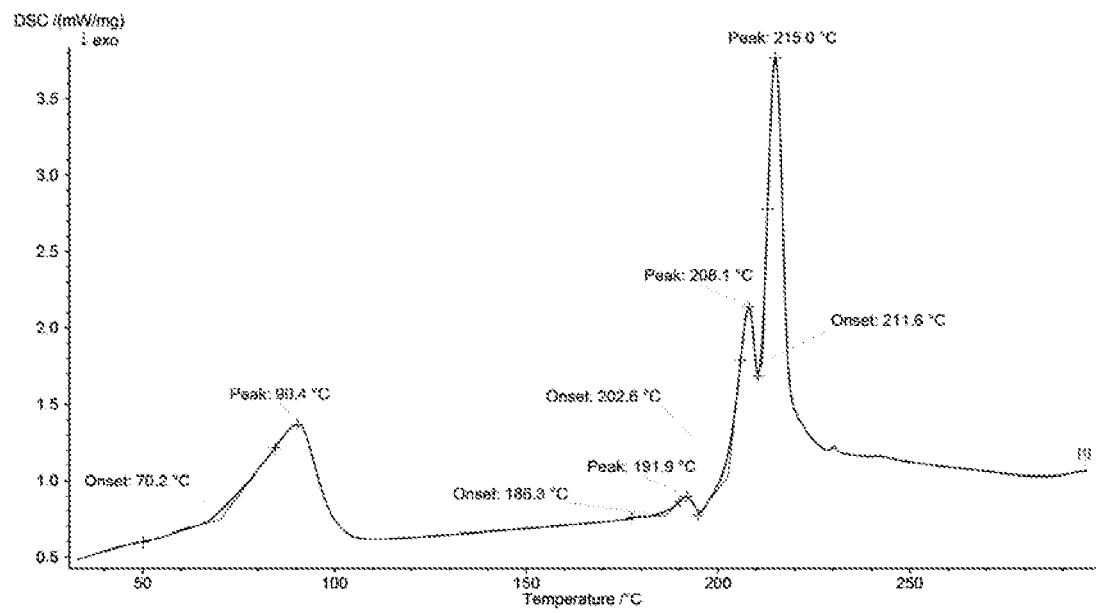
FIG. 15 shows a differential scanning calorimetry (DSC) profile of Form C-II of hydrate of salt of Formula A, wherein the horizontal axis (X-axis) plots the temperature (° C.), and the vertical axis (Y-axis) plots the heat flow (mW).

In some embodiments, Form C-II of hydrate of salt of Formula A may be characterized by differential scanning calorimetry (DSC). In some embodiments, Form C-II of hydrate of salt of Formula A has a DSC curve as shown in FIG. 15. In the DSC profile, the endothermic peaks of Form C-II of hydrate of salt of Formula A are at about 70.2-90.4° C. and about 202.6-215.0° C.

Figure 16:
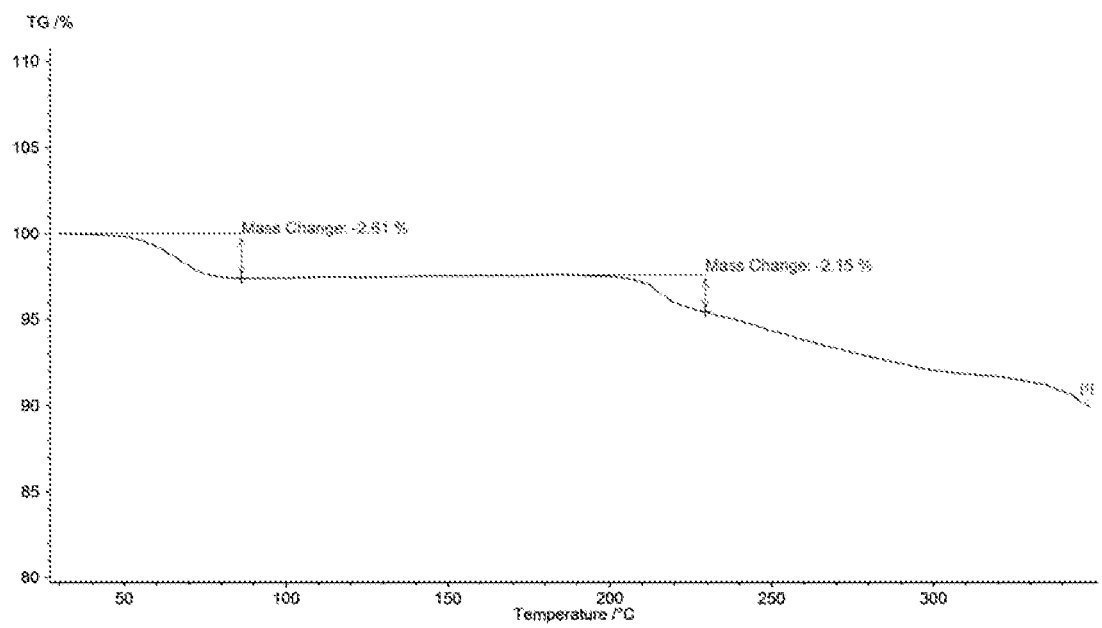
FIG. 16 shows a Thermogravimetric (TG) profile of Form C-II of hydrate of salt of Formula A, wherein the horizontal axis (X-axis) plots the temperature (° C.), and the vertical axis (Y-axis) plots the weight percentage (%).

In some embodiments, Form C-II of hydrate of salt of Formula A may be characterized by thermogravimetric analysis (TGA). In some embodiments, Form C-II of hydrate of salt of Formula A has a TGA curve as shown in FIG. 16, indicating that the weight loss near 30-90° C. is 2.61%, Form C-II is a hydrate containing 0.75 molecule of water.

In some embodiments, Form C-II of hydrate of salt of Formula A is substantially free of other crystalline forms as described herein. For example, the content by weight of Form C-II of hydrate of salt of Formula A is at least 99%, at least 95%, at least 90%, or even lower to 80%. Further, the content by weight of Form C-II of hydrate of salt of Formula A is at least 70%, or at least 60%. Even further, the content by weight of Form C-II of hydrate of salt of Formula A is at least 50%.

Methods of Preparing Form C-II

The present invention relates to the method of preparing Form C-II of hydrate of salt of Formula A, comprising:

(1) reacting the compound (S)-7-(4-(1-(methylsulfonyl)piperidin-4-yl)phenyl)-N-(morpholin-2-ylmethyl)pyrido[3, 4-b]pyrazin-5-amine with malic acid to form a salt, which is stirred in a mixed solvent consisting of acetonitrile and water;

(2) isolating to obtain the solid Form C-II of (S)-7-(4-(1-(methylsulfonyl)piperidin-4-yl) phenyl)-N-(morpholin-2-ylmethyl)pyrido[3,4-b]pyrazin-5-amine malate;

(3) optionally drying the solid obtained in step (2).

In some embodiments, the mole ratio of malic acid to compound (S)-7-(4-(1-(methylsulfonyl)piperidin-4-yl)phenyl)-N-(morpholin-2-ylmethyl)pyrido[3,4-b]pyrazin-5-amine is no less than about 1:1. In some embodiments, the mole ratio is about 1.1:1.

In some embodiments, the ratio of the volume (mL) of the mixed solvent to the weight (g) of compound (S)-7-(4-(1-(methylsulfonyl)piperidin-4-yl)phenyl)-N-(morpholin-2-ylmethyl) pyrido[3,4-b]pyrazin-5-amine in step (1) is about 88 mL/g (volume/weight ratio).

In some embodiments, the volume ratio of water to acetonitrile in step (1) is no less than about 6:1. In some embodiments, the volume ratio is about 6:1.

In some embodiments, in step (1), the salt is formed under heating and/or stirring. The heating temperature is not higher than the boiling point of the solvent system, such as about 80-85° C.

In some embodiments, in step (1), the formed salt is stirred under cooling, preferably cooling naturally, such as cooling to room temperature.

In some embodiments, in step (1), the formed salt is stirred for 1-120 hours, such as at least 18 hours.

Hydrate (Form C-III)

The present invention further provides hydrate of salt of Formula A (wherein, n is 0.5, M is malic acid).

In some embodiments, hydrate of salt of Formula A (wherein, n is 0.5, M is malic acid) is monohydrate.

In some embodiments, monohydrate of salt of Formula A (wherein, n is 0.5, M is malic acid) is Form C-III.

In some embodiments, Form C-III of monohydrate of salt of Formula A may be characterized through X-ray powder diffraction. The X-ray powder diffraction characteristic diffraction angles (2θ) of Form C-III include 5.3, 10.6, 17.0, 17.9, and 25.2 degrees, the measured 2θ values each having an error of about 0.2 degrees (2θ).

In some embodiments, the X-ray powder diffraction characteristic diffraction angles (2θ) of Form C-III of monohydrate of salt of Formula A include 5.3, 10.6, 12.8, 17.0, 17.9, 20.3, 21.7, 22.5, and 25.2 degrees, the measured 2θ values each having an error of about ±0.2 degrees (2θ).

In some embodiments, the X-ray powder diffraction characteristic diffraction angles (2θ) of Form C-III of monohydrate of salt of Formula A include 5.3, 10.6, 11.8, 12.8, 16.0, 17.0, 17.9, 18.9, 20.3, 21.7, 22.5, and 25.2 degrees, the measured 2θ values each having an error of about ±0.2 degrees (2θ).

In some embodiments, the X-ray powder diffraction characteristic diffraction angles (2θ) of Form C-III of monohydrate of salt of Formula A include 5.3, 10.6, 11.8, 12.8, 16.0, 17.0, 17.9, 18.6, 18.9, 20.3, 21.7, 22.5, 23.1, 25.2, 25.6, and 27.4 degrees, the measured 2θ values each having an error of about ±0.2 degrees (2θ).

Figure 17:
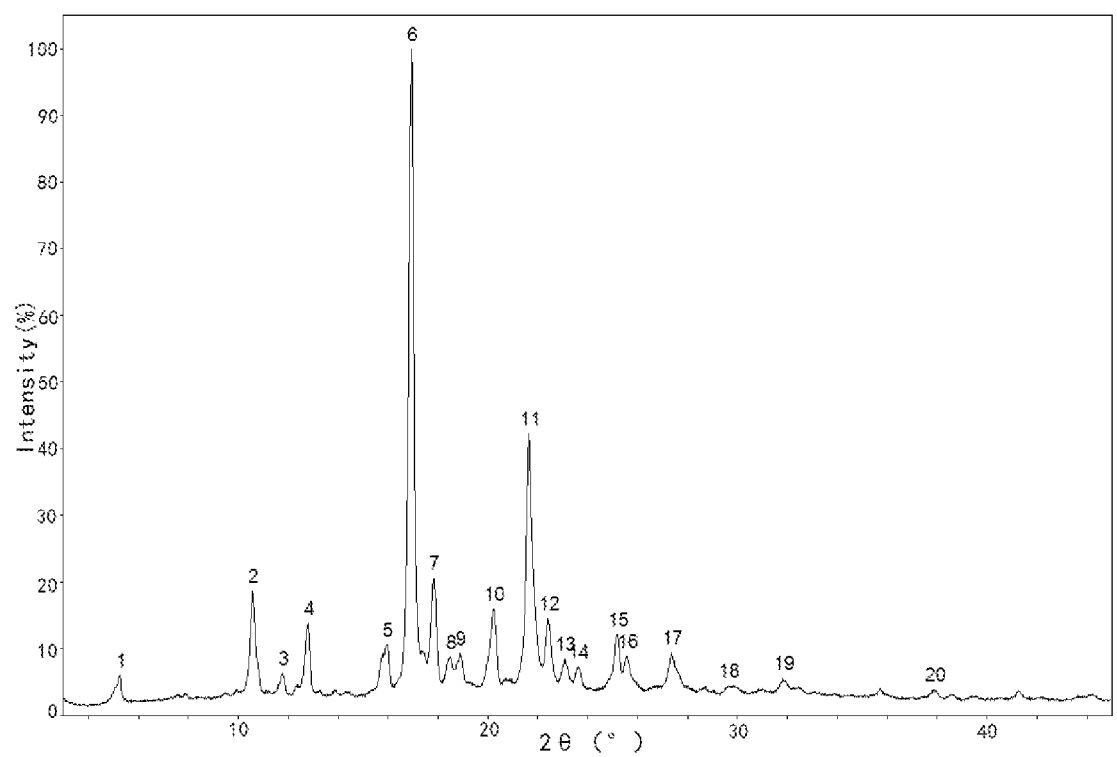
FIG. 17 shows an X-ray powder diffractogram of Form C-III of monohydrate of salt of Formula A, wherein the horizontal axis (X-axis) plots the diffraction angle 2 theta, and the vertical axis (Y-axis) plots the diffraction intensity (%).

In some embodiments, Form C-III of monohydrate of salt of Formula A has a diffractogram as shown in FIG. 17. Despite of experimental errors, instrument errors, preferred orientation and the like, one skilled in the art can obtain sufficient information from the XRPD data provided herein to identify Form C-III of monohydrate of salt of Formula A.

Figure 18:
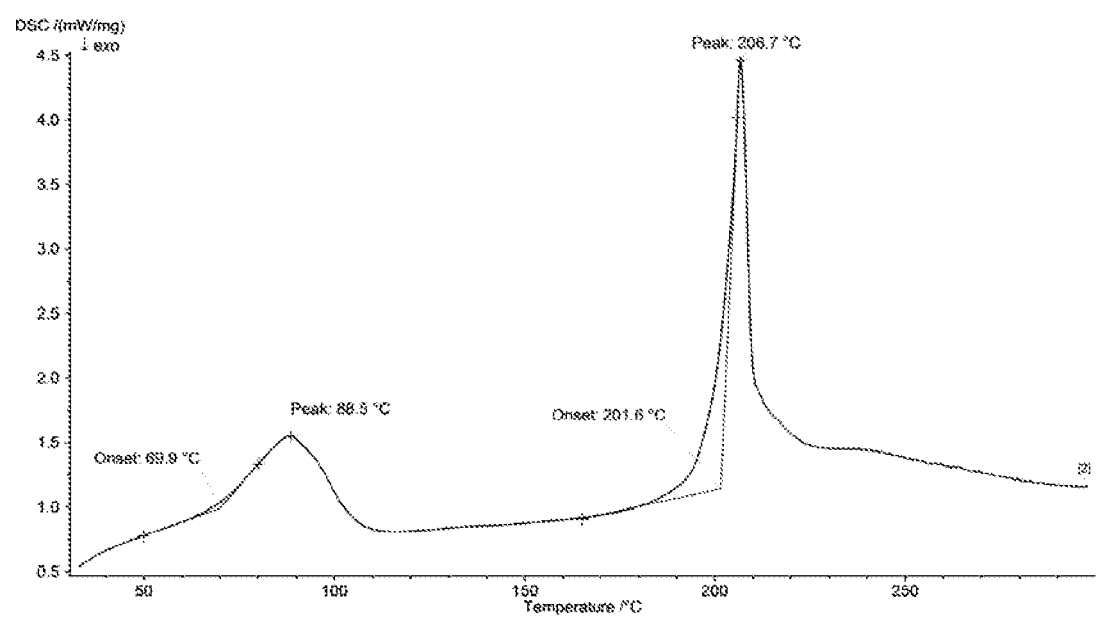
FIG. 18 shows a differential scanning calorimetry (DSC) profile of Form C-III of monohydrate of salt of Formula A, wherein the horizontal axis (X-axis) plots the temperature (° C.), and the vertical axis (Y-axis) plots the heat flow (mW).

In some embodiments, Form C-III of monohydrate of salt of Formula A may be characterized by differential scanning calorimetry (DSC). In some embodiments, Form C-III of monohydrate of salt of Formula A has a DSC curve as shown in FIG. 18. In the DSC profile, the endothermic peaks of Form C-III of monohydrate of salt of Formula A are at about 69.9-88.5° C. and about 201.6-206.7° C.

Figure 19:
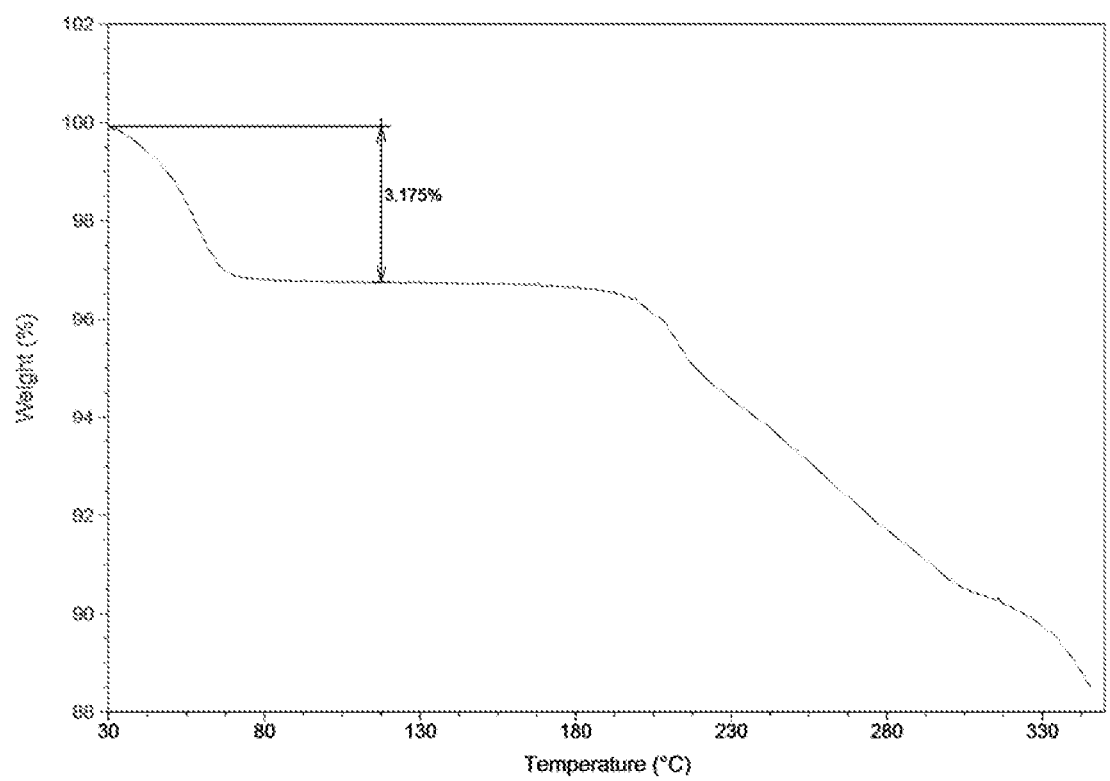
FIG. 19 shows a Thermogravimetric (TG) profile of Form C-III of monohydrate of salt of Formula A, wherein the horizontal axis (X-axis) plots the temperature (° C.), and the vertical axis (Y-axis) plots the weight percentage (%).

In some embodiments, Form C-III of monohydrate of salt of Formula A may be characterized by thermogravimetric analysis (TGA). In some embodiments, Form C-III of monohydrate of salt of Formula A has a TGA curve as shown in FIG. 19, indicating that the weight loss near 30-90° C. is 3.2%. Form C-III is a monohydrate.

In some embodiments, Form C-III of monohydrate of salt of Formula A is substantially free of other crystalline forms as described herein. For example, the content by weight of Form C-III of monohydrate of salt of Formula A is at least 99%, at least 95%, at least 90%, or even lower to 80%. Further, the content by weight of Form C-III of monohydrate of salt of Formula A is at least 70%, or at least 60%. Even further, the content by weight of Form of monohydrate of salt of Formula A is at least 50%.

Methods of Preparing Form C-III

The present invention relates to the method of preparing Form C-III of hydrate of salt of Formula A, comprising:

(1) reacting the compound (S)-7-(4-(1-(methylsulfonyl) piperidin-4-yl)phenyl)-N-(morpholin-2-ylmethyl)pyrido[3,4-b]pyrazin-5-amine with malic acid to form a salt, which is stirred in a mixed solvent consisting of ethanol and water;

(2) isolating to obtain the solid Form C-III of (S)-7-(4-(1-(methylsulfonyl)piperidin-4-yl) phenyl)-N-(morpholin-2-ylmethyl)pyrido[3,4-b]pyrazin-5-amine malate;

(3) optionally drying the solid obtained in step (2).

In some embodiments, the mole ratio of malic acid to compound (S)-7-(4-(1-(methylsulfonyl)piperidin-4-yl)phenyl)-N-(morpholin-2-ylmethyl)pyrido[3,4-b]pyrazin-5-amine is no less than about 1:1. In some embodiments, the mole ratio is about 1.5:1.

In some embodiments, the ratio of the volume (mL) of the mixed solvent to the weight (g) of compound (S)-7-(4-(1-(methylsulfonyl)piperidin-4-yl)phenyl)-N-(morpholin-2-ylmethyl) pyrido[3,4-b]pyrazin-5-amine in step (1) is about 55 mL/g (volume/weight ratio).

In some embodiments, the volume ratio of water to ethanol in step (1) is no less than about 4:1. In some embodiments, the volume ratio is about 4:1.

In some embodiments, in step (1), the salt is formed under heating and/or stirring. The heating temperature is not higher than the boiling point of the solvent system, such as about 80° C.

In some embodiments, in step (1), the formed salt is stirred under cooling, preferably cooling naturally, such as cooling to room temperature or lower temperature, e.g. about 15-20° C.

In some embodiments, in step (1), the formed salt is stirred for 1-120 hours, such as at least 12 hours.

The features of each embodiment for above methods of preparing the crystalline forms of salt of Formula A or its solvates can be arbitrary combined. Each embodiment obtained from such arbitrary combinations is included within the scope of the present invention, as if these embodiments obtained from such arbitrary combinations are specifically and individually listed herein.

Pharmaceutical Compositions and Methods of Treatment

Salt of Formula A or its solvates, or the crystalline forms of salt of Formula A or its solvates (such as Form A-I, Form B-I, Form B-II, Form C-I, Form C-II, and Form C-III) are useful in the treatment of diseases, such as autoimmune diseases, inflammatory diseases, and cancer. The cancer is preferably hematological malignancy. The autoimmune diseases, inflammatory diseases, and cancer include but not limited to systemic lupus erythematosus, rheumatoid arthritis, Sjorgen's syndrome, IgA nephropathy, autoimmune hemolytic anemia, idiopathic thrombocytopenic purpura, multiple sclerosis, myasthenia gravis, allergic rhinitis, chronic obstructive pulmonary disease, adult respiratory distress syndrome, asthma, lymphoma (such as B cell lymphoma, T cell lymphoma), leukemia (such as chronic lymphocytic leukemia, acute lymphocytic leukemia, and acute myeloid leukemia), and multiple myeloma.

The present invention provides the method of treating diseases responsive to inhibition of Syk kinase activity, comprises administering the active pharmaceutical ingredients consisting of salt of Formula A, or one or more of salt of Formula A or its solvates or the crystalline forms of salt of Formula A or its solvates, such as Form A-I, Form B-I, Form B-II, Form B-III, Form C-I, Form C-II, or Form C-III.

In some embodiments, the treatment method is directed to at least one disease responsive to inhibition of Syk kinase activity, such as autoimmune diseases, inflammatory diseases, and cancer (preferably hematological malignancy). An effective amount of a pharmaceutical composition of the present invention is administered to a subject in need thereof, wherein the pharmaceutical composition comprises at least one pharmaceutically acceptable carrier and one or more of salt of Formula A or its solvates or the crystalline forms of salt of Formula A or its solvates (such as Form A-I, Form B-II, Form B-III, Form C-I, Form C-II, or Form C-III).

The dosing amount of the at east one active pharmaceutical ingredient selected from salt of Formula A, or the crystalline forms of salt of Formula A, or the solvates of salt of Formula A or the crystalline forms thereof (such as Form A-I, Form B-I, Form B-II, Form B-III, Form Form C-II, or Form C-III) to achieve the desired biological effect may depend on a number of factors, e.g., the intended use, the mode of administration, and the clinical condition of the patient. The daily dose may, for example, range from 0.01 mg to 3 g/day (such as from 0.05 mg to 2 g/day, even from 100 mg to 1 g/day). Unit dose formulations which can be administered orally include, for example, tablets or capsules.

For the therapy of the above-mentioned conditions, the at least one active pharmaceutical ingredient selected from salt of Formula A or its solvates or the crystalline forms of salt of Formula A or its solvates may be administered as such, hut typically in the form of a pharmaceutical composition formulated with one or more pharmaceutically acceptable carriers or excipients.

Representative carriers or excipients should be compatible with the other ingredients of the composition and do not have harmful effect on the patient's health. The carrier or excipient may be a solid or a liquid or both, and may be formulated with salt of Formula A or its solvates or the crystalline forms of salt of Formula A or its solvates (such as Form A-I, Form B-I, Form B-II, Form B-III, Form C-I, Form C-II, and/or Form C-III) into a pharmaceutical composition or a unit dosage form (for example, a tablet, a capsule), which may contain from 0.05% to 95% by weight of salt of Formula A. The pharmaceutical compositions described herein can be produced by known pharmaceutical methods, such as those involving mixing with pharmaceutically acceptable carriers and/or excipients and diluents.

In some embodiments, the at least one active pharmaceutical ingredient selected from salt of Formula A or its solvates or the crystalline forms of salt of Formula A or its solvates (such as Form A-I, Form B-I, Form B-II, Form C-I, Form C-II, and Form C-III) may be combined with at least one component, such as carrier and/or excipient and/or diluent, which may be selected from sweeteners, flavoring agents, coloring agents, dyes, and emulsifiers.

In some embodiments, the conversion of salt of Formula A or its solvates or the crystalline forms of salt of Formula A or its solvates (such as Form A-I, Form B-I, Form B-II, Form B-III, Form C-I, Form C-II, and Form C-III) will not occur when formulating with the one or more pharmaceutically acceptable carriers and/or excipients and/or diluents. In other embodiments, salt of Formula A or its solvates or the crystalline forms of salt of Formula A or its solvates (such as Form A-I, Form B-I, Form B-II, Form B-III, Form C-I, Form C-II, or Form C-III) may be converted, in whole or in part, to one or more other forms, including a non-solid form, when formulating with the one or more pharmaceutically acceptable carriers and/or excipients and/or diluents. In some embodiments, Form A-I or other forms described herein can be dissolved when formulated into a pharmaceutical composition. Accordingly, in such "dissolved" cases, Form A-I or other forms no longer exists in their respective crystalline forms in the pharmaceutical composition.

In some embodiments, the at least one active pharmaceutical ingredient selected from salt of Formula A or its solvates or the crystalline forms of salt of Formula A or its solvates (such as Form A-I, Form B-I, Form B-II, Form B-III, Form C-I, Form C-II, and Form C-III) is formulated into a suitable dosage form.

Pharmaceutical compositions described herein may be dosage forms suitable for oral and peroral (for example sublingual) administration. The suitable mode of administration may depend on not only the condition in each individual case and severity of the condition to be treated, but also the nature of the specific forms of the active pharmaceutical ingredient selected from salt of Formula A or its solvates or the crystalline forms of salt of Formula A or its solvates (such as Form A-I, Form B-I, Form B-II, Form B-III, Form C-I, Form C-II, and Form C-III) used in preparing the pharmaceutical composition.

Suitable pharmaceutical compositions for oral administration prepared from the at least one active pharmaceutical ingredient selected from salt of Formula A or its solvates or the crystalline forms of salt of Formula A or its solvates (such as Form A-I, Form B-I, Form B-II, Form B-III, Form C-I, Form C-II, and Form C-III) may be in the form of unit dosage forms such as capsules, cachets, and tablets, including suckable tablets, each of which is prepared with a defined amount of the at least one active pharmaceutical ingredient described herein; as well as in the forms selected from powders, granules, solutions, suspensions in an aqueous or nonaqueous liquid, and oil-in-water and water-in-oil emulsions. Those compositions may, as already mentioned, be prepared by any suitable pharmaceutical formulation methods, such as those including a step wherein the at least one active pharmaceutical ingredient selected from salt of Formula A or its solvates or the crystalline forms of salt of Formula A or its solvates (such as Form A-I, Form B-I, Form B-II, Form B-III, Form C-I, Form C-II, and Form C-III) and a carrier and/or excipient and/or diluent (which may consist of one or more added ingredients) are brought into contact. The compositions can generally be produced by uniformly and homogeneously mixing the at least one active pharmaceutical ingredient selected from salt of Formula A or its solvates or the crystalline forms of salt of Formula. A or its solvates (such as Form A-I, Form B-I, Form B-II, Form B-III, Form C-I, Form C-II, and Form C-III) with liquid or finely divided solid carriers, after which the product can be shaped.

The at least one active pharmaceutical ingredient selected from salt of Formula A or its solvates or the crystalline forms of salt of Formula A or its solvates (such as Form A-I, Form B-I, Form B-II, Form C-I, Form C-II, and Form C-III) can also be administered in combination with one or more other active ingredients (such as in the synergetic therapy). When administered as a combination, the active ingredients can be formulated as separate compositions that are administered at the same time or sequentially at different times (such as administered sequentially in any orders) through the same or different administration routes, or the active ingredients can be administered in the same pharmaceutical composition.

In some embodiments, the at least one active pharmaceutical ingredient selected from salt of Formula A or its solvates or the crystalline forms of salt of Formula A or its solvates (such as Form A-I, Form B-I, Form B-II, Form B-III, Form C-I, Form C-II, and Form C-III) can be administered in combination with one or more other active ingredients with known therapeutic effect, for example for the treatment of diseases responsive to inhibition of Syk kinase activity, such as autoimmune diseases, inflammatory diseases, and cancer (preferably hematological malignancy).

The phrase "combination", as described herein, defines the combined use of the at least one active pharmaceutical ingredient selected from salt of Formula A or its solvates or the crystalline forms of salt of Formula A or its solvates (such as Form A-I, Form B-I, Form B-II, Form B-III, Form C-I, Form C-II, and Form C-III) with one or more other active ingredients, such as, the combined use in the treatment of autoimmune diseases or inflammatory diseases (for example, in combination with immunosuppressants, steroids), the combined use in the anti-neoplastic method (for example, in combination with BTK inhibitors, PI3Kδ inhibitors, Bcl-2 inhibitors, Lenalidomide). Examples of BTK inhibitors include but not limited to Ibrutinib, ACP-196 (Acalabrutinib), CC-292 (Spebrutinib), ONO-4059 (Tirabrutinib), BGB-3111, and GDC-0853. Examples of PI3Kδ inhibitors include but not limited to Idelalisib, IPI-145 (Duvelisib), TGR-1202 (Umbralisib), GS-9820 (Acalisib), and INCB-050465. Examples of Bcl-2 inhibitors include but not limited to Venetoclax (ABT-199) and ABT-263 (Navitoclax). As used herein, the term "anti-neoplastic method" refers to any method for purposes of treating the cancer (including hematological malignancy). Examples of anti-neoplastic method include but not limited to: chemotherapy, radiotherapy, targeted therapy, and immunotherapy.

Examples of immunosuppressants include but not limited to corticosteroids (e.g., fluticasone propionate, beclomethasone dipropionate, mometasone furoate, triamcinolone acetonide, or budesonide), disease-modifying agents (e.g., antimalarials, methotrexate, sulfasalazine, mesalamine, azathioprine, 6-mercaptopurine, metronidazole, or D-penicillamine); non-steroidal anti-inflammatory drugs (e.g., acetaminophen, aspirin, sodium salicylate, sodium cromoglycate, magnesium salicylate, choline magnesium salicylate, salicylsalicylic acid, ibuprofen, naproxen, diclofenac, diflunisal, etodolac, fenoprofen calcium, flurbiprofen, piroxicam, indomethacin, ketoprofen, ketorolac tromethamine, meclofenamate, meclofenamate sodium, mefenamic acid, nabumetone, oxaprozin, phenyl butyl nitrone (PBN), sulindac, or tolmetin), COX-2 inhibitors, inhibitors of cytokine synthesis/release (e.g., anti-cytokine antibodies, anti-cytokine receptor antibodies, and the like).

Thus, methods described herein are not limited by the sequence of administration; the one or more other active ingredients may be administered simultaneously to, prior to or after the administration of the at least one active pharmaceutical ingredient. The at least one active pharmaceutical ingredient in the combination described above is selected from salt of Formula A or its solvates or the crystalline forms of salt of Formula A or its solvates (such as Form A-I, Form B-I, Form B-II, Form B-III, Form C-I, Form C-II, and Form C-III).

The following non-limiting examples are provided.

Experiments

The compound (S)-7-(4-(1-(methylsulfonyl)piperidin-4-ylphenyl)-N-(morpholin-2-yl methyl)pyrido[3,4-b]pyrazin-5-amine raw material used in the examples were prepared according to WO2012167733A1.

All reagents, except intermediates, used in this disclosure are commercially available. The names of all compounds, except the reagents, were generated by ChemBioDraw Ultra 16.0.

Unless otherwise indicated, X-ray powder diffractograms were obtained using Germany Bruker D8 ADVANCE X-ray diffractometer (target: Cu; voltage: 40 kV; electric current: 40 mA; scanning speed: 4 degrees/min; step size: 0.02 degree; scanning range: 3-45 degrees).

Unless otherwise indicated, differential scanning calorimetry (DSC) were performed on Germany NETZSCH DSC 204F1 (purge gas: nitrogen; flow rate: 20-60 mL min$^{-1}$; heating rate: 5-10° C./min; temperature range: 30° C. to 300° C.). The samples were measured in the pricked aluminum pans. Indium was used for temperature calibration.

Unless otherwise indicated, thermogravimetric (TG) analyses were obtained using Germany NETZSCH TGA 209F1 (purge gas: nitrogen; heating rate: 10° C./min).

Differential scanning calorimetry (DSC) and thermogravimetric (TG) analysis of FIGS. 8 and 10 were performed on DSC Q2000 and TG Q500 of American TA company respectively.

EXAMPLE 1

Preparation of Form A-I of Salt of Formula A (S)-7-(4-(1-(methylsulfonyl)piperidin-4-yl)phenyl)-N-(morpholin-2-ylmethyl)pyrido[3,4-b] pyrazin-5-amine (100 mg, 0.21 mmol) was suspended in 1 mL of ethanol, and heated to reflux slightly under stirring. Then 0.315 mL of 1M acetic acid aqueous solution was added to obtain a clear solution, and heating was stopped. Then the solution was stirred at room temperature for 5 days. Then the precipitate was filtered out and dried to give 71.52 mg of yellow solid.

$^1$H NMR (400 MHz, cdcl3) δ 8.88 (d, J=1.9 Hz, 1H), 8.59 (d, J=1.9 Hz, 1H), 8.12 (d, J=8.3 Hz, 2H), 7.53 (s, 1H), 7.33 (d, J=8.3 Hz, 2H), 7.07 (t, J=5.6 Hz, 1H), 4.06-3.94 (m, 4H), 3.89 (tdd, J=6.6, 3.9, 2.4 Hz, 1H), 3.70 (dtd, J=10.9, 6.9, 4.5 Hz, 2H), 3.11 (dd, J=12.3, 2.0 Hz, 2H), 2.93 (dd, J=10.4, 3.0 Hz, 2H), 2.85 (d, J=1.7 Hz, 3H), 2.83-2.75 (m, 2H), 2.74-2.63 (m, 1H), 2.05 (s, 2H), 2.02 (d, J=13.9 Hz, 2H), 1.97-1.83 (m, 2H).

The obtained powder sample is Form of salt of Formula A, the X-ray powder diffractogram of which is shown in FIG. 1. Peaks (2θ) chosen from the figure have the following values: 6.2, 9.4, 10.8, 12.1, 14.1, 15.8, 16.3, 17.2, 19.0, 19.3, 20.1, 21.1, 21.7, 22.2, 22.7, 24.6, 25.4, 26.8, 27.2, 27.5, 29.2, 30.6, and 31.8 degrees, the measured 2θ values each having an error of about ±0.2 degrees (2θ), wherein characteristic peaks (2θ) are at 6.2, 9.4, 16.3, 17.2, and 19.0 degrees. DSC result is given in FIG. 2, showing that Form A-I has obvious endothermic peaks at about 162.8-179.6° C. and about 217.0-219.4° C.

EXAMPLE 2

Preparation of Form A-I of Salt of Formula A

Glacial acetic acid (0.124 mL, 2.1 mmol) and (S)-7-(4-(1-(methylsulfonyl)piperidin-4-yl)phenyl)-N-(morpholin-2-ylmethyl)pyrido[3,4-b]pyrazin-5-amine (100 mg, 0.21 mmol) were added into 2 mL of ethanol, and heated to dissolve under stirring, after which heating was stopped. Then 0.5 mL of isopropyl ether was added, and the stirring was continued at room temperature overnight. Then the precipitate was filtered out and dried to give 60 mg of yellow solid. Upon measurement, the X-ray powder diffractogram of the obtained sample is consistent with that of Form A-I of salt of Formula A obtained in Example 1.

EXAMPLE 3

Preparation of Form Salt of Formula A (S)-7-(4-(1-(methylsulfonyl)piperidin-4-yl)phenyl)-N-morpholin-2-ylmethyl)pyrido[3,4-b] pyrazin-5-amine (100 mg, 0.21 mmol) and 0.5 mL of 1M acetic acid aqueous solution were mixed in 95% ethanol (5 mL), and heated to dissolve under stirring, after which the mixed solution was cooled to room temperature. Then 0.2 mL of isopropyl ether was added, and stirred at room temperature overnight. Then the precipitate was filtered out and dried to give 20 mg of yellow solid. Upon measurement, the X-ray powder diffractogram of the obtained sample is consistent with that of Form A-I of salt of Formula A obtained in Example 1.

EXAMPLE 4

Preparation of Form A-I of Salt of Formula A (S)-7-(4-(1-(methylsulfonyl)piperidin-4-yl)phenyl)-N-morpholin-2-ylmethyl)pyrido[3,4-b] pyrazin-5-amine (1.0 g, 2.1 mmol) was added into 4 mL of ethanol, and heated to 50-55° C. under stirring. Then 3 mL of glacial acetic acid was added to obtain a clear solution. Then 9 mL of methyl tert-butyl ether was added dropwise. After keeping warm at 50-55° C. for 30 minutes, the solution was cooled to 20-25° C., and stirred for another 17 hours. Then the precipitate was filtered out and dried at 55° C. under vacuum for 5 hours to give 0.98 g of product, yield 87%, purity 99.55%. Upon measurement, the X-ray powder diffractogram of the obtained sample is consistent with that of Form A-I of salt of Formula A obtained in Example 1.

EXAMPLE 5

Preparation of Form A-I of Salt of Formula A (S)-7-(4-(1-(methylsulfonyl)piperidin-4-yl)phenyl)-N-morpholin-2-ylmethyl)pyrido[3,4-b] pyrazin-5-amine (4.0 g, 8.29 mmol) was added into a mixed solvent, consisting of 16 mL of ethanol and 10 mL of water, and heated to 70-75° C. under stirring. Then 1.42 mL of glacial acetic acid was added to obtain a clear solution. Then 100 ml, of ethanol was added slowly. After keeping warm at 70-75° C. under stirring for 30 minutes, the solution was cooled to 0-5° C. slowly. Then the precipitate was filtered out and dried at 55° C. under vacuum tor 17 hours to give 3.8 g of product, yield 84%, purity 99.77%. Upon measurement, the X-ray powder diffractogram of the obtained sample is consistent with that of Form A-I of salt of Formula A obtained in Example 1.

EXAMPLE 6

Preparation of Form A-I of Salt of Formula A (S)-7-(4-(1-(methylsulfonyl)piperidin-4-yl)phenyl)-N-(morpholin-2-ylmethyl)pyrido[3,4-b] pyrazin-5-amine (1.0 g, 2.1 mmol) was added into 4 mL of i-propanol, and heated to 50-55° C. under stirring. Then 3 mL of glacial acetic acid was added to obtain a clear solution. Then 9 mL of methyl tert-butyl ether was added dropwise. After keeping warm at 50-55° C. for 30 minutes, the solution was cooled to 20-25° C., and stirred for another 17 hours. Then the precipitate was filtered out and dried at 55° C. under vacuum for 5 hours to give 0.99 g of product, yield 88%, purity 99.54%. Upon measurement, the X-ray powder diffractogram of the obtained sample is consistent with that of Form A-I of salt of Formula A obtained in Example 1.

EXAMPLE 7

Preparation of Form A-I of Salt of Formula A (S)-7-(4-(1-(methylsulfonyl)piperidin-4-yl)phenyl)-N-morpholin-2-ylmethyl)pyrido[3,4-b] pyrazin-5-amine (48 mg, 0.1 mmol) was suspended in 4 mL of i-propanol, and heated to 80° C. under stirring. Then 0.32 mL of 1M acetic acid aqueous solution was added to obtain a clear solution. Then the solution was stirred overnight after cooling to room temperature. Then the precipitate was filtered out and dried to give 40 mg of solid. Upon measurement, the X-ray powder diffractogram of the obtained sample is consistent with that of Form A-I of salt of Formula A obtained in Example 1.

EXAMPLE 8

Preparation of Form A-I of Salt of Formula A (S)-7-(4-(1-(methylsulfonyl)piperidin-4-yl)phenyl)-N-(morpholin-2-ylmethyl)pyrido[3,4-b] pyrazin-5-amine (1.0 g, 2.1 mmol) was suspended in 10 mL of i-propanol, and heated to 80-85° C. Then 3.11 mL of 1M acetic acid aqueous solution was added to obtain a clear solution. Then 10 mL of i-propanol was added, and the reaction system was cooled to room temperature and stirred overnight. Then the precipitate was collected by filtration, washed with i-propanol, and dried at 60° C. under vacuum for 2 hours to give 880 mg of product, purity 99.2%. Upon measurement, the X-ray powder diffractogram of the obtained sample is consistent with that of Form A-I of salt of Formula A obtained in Example 1.

EXAMPLE 9

Preparation of Form A-I of Salt of Formula A (S)-7-(4-(1-(methylsulfonyl)piperidin-4-yl)phenyl)-N-morpholin-2-ylmethyl)pyrido[3,4-b] pyrazin-5-amine (100 mg, 0.21 mmol) was suspended in 1 mL, of acetonitrile, and heated to reflux slightly under stirring. Then 0.315 mL of 1M acetic acid aqueous solution was added to obtain a clear solution. Heating was stopped, and stirring was performed at room temperature overnight. Then 1 mL of acetonitrile was added, and the stirring was continued for 5 days. Then the precipitate was filtered out and dried to give 38.54 mg of yellow solid. Upon measurement, the X-ray powder diffractogram of the obtained sample is consistent with that of Form A-I of salt of Formula A obtained in Example 1.

EXAMPLE 10

Preparation of Form A-I of Salt of Formula A (S)-7-(4-(1-(methylsulfonyl)piperidin-4-yl)phenyl)-N-(morpholin-2-ylmethyl)pyrido[3,4-b] pyrazin-5-amine (48 mg, 0.1 mmol) was suspended in 4.5 mL of acetonitrile, and heated to 80-85° C. Then 0.2 mL of 1M acetic acid aqueous solution and 0.1 mL of water were added to obtain a clear solution. Then the reaction system was cooled to room temperature and stirred overnight. Then the precipitate was collected by filtration, and dried to give 39.4 mg of product. Upon measurement, the X-ray powder diffractogram of the obtained sample is consistent with that of Form A-I of salt of Formula A obtained in Example 1.

EXAMPLE 11

Preparation of Form A-I of Salt of Formula A (S)-7-(4-(1-(methylsulfonyl)piperidin-4-yl)phenyl)-N-(morpholin-2-ylmethyl)pyrido[3,4-b] pyrazin-5-amine (100 mg, 0.21 mmol) was suspended in 1 mL of acetone, and heated to reflux slightly. Then 0.315 mL of 1M acetic acid aqueous solution was added to obtain a clear solution, and heating was stopped. Then the reaction system was stirred at room temperature overnight, and the product was precipitated. Stirring was continued at room temperature for another 5 days. Then the precipitate was collected by filtration, and dried at room temperature to give 76.04 mg of product. Upon measurement, the X-ray powder diffractogram of the obtained sample is consistent with that of Form A-I of salt of Formula A obtained in Example 1.

EXAMPLE 12

Preparation of Form A-I of Salt of Formula A (S)-7-(4-(1-(methylsulfonyl)piperidin-4-yl)phenyl)-N-morpholin-2-ylmethyl)pyrido[3,4-b] pyrazin-5-amine (1.0 g, 2.1 mmol) was dissolved in 3 mL of glacial acetic acid at 60-64° C. Then 18 mL of t-butanol was added dropwise, after which the stirring was continued for 30 minutes. After cooling to 20-25° C., the solution was stirred for another 17 hours. Then the precipitate was collected by filtration and dried at 60° C. under vacuum for 6 hours to give 1.04 g of product, yield 92%, purity 98.74%. Upon measurement, the X-ray powder diffractogram of the obtained sample is consistent with that of Form A-I of salt of Formula A obtained in Example 1.

EXAMPLE 13

Preparation of Form A-I of Salt of Formula A (S)-7-(4-(1-(methylsulfonyl)piperidin-4-yl)phenyl)-N-(morpholin-2-ylmethyl)pyrido[3,4-b] pyrazin-5-amine (1.0 g, 2.1 mmol) was suspended in a mixed solvent consisting of 6 mL of dioxane and 2 mL of water, and heated to 45-50° C. under stirring. Then 0.36 mL of glacial acetic acid was added to obtain a clear solution. Then 10 mL of dioxane was added at 50-55° C. Then the reaction system was cooled to 20-25° C., and stirred for another 2 hours. Then the precipitate was collected by filtration and dried at 55° C. under vacuum to give 0.7 g of product, yield 62%, purity 99.83%. Upon measurement, the X-ray powder diffractogram of the obtained sample is consistent with that of Form A-I of salt of Formula A obtained in Example 1.

EXAMPLE 14

Preparation of Form A-I of Salt of Formula A (S)-7-(4-(1-(methylsulfonyl)piperidin-4-yl)phenyl)-N-(morpholin-2-ylmethyl)pyrido[3,4-b] pyrazin-5-amine (1.0 g, 2.1 mmol) was dissolved in 3 mL of glacial acetic acid at 40-50° C. Then 35 mL of dioxane was added dropwise, after which the reaction system was cooled to 20-25° C. and stirred for 1 hour. Then the cooling was continued to 5-10° C., and the stirring was performed for 1 hour. Then the precipitate was collected by filtration and dried at 55° C. under vacuum for 17 hours to give 0.23 g of product. Upon measurement, the X-ray powder diffractogram of the obtained sample is consistent with that of Form A-I of salt of Formula A obtained in Example 1.

EXAMPLE 15

Preparation of Form A-I of Salt of Formula A (S)-7-(4-(1-(methylsulfonyl)piperidin-4-yl)phenyl)-N-(morpholin-2-ylmethyl)pyrido[3,4-b] pyrazin-5-amine (0.5 g, 1.04 mmol) was dissolved in 9.5 mL of dichloromethane at 40-45° C., and 0.12 mL of glacial acetic acid was added under stirring. Then 3 mL of methyl tert-butyl ether was added. After keeping warm at 40-45° C. and stirring for 10 minutes, the solution was cooled to 20-25° C., and stirred for another 1 hours. Then the precipitate was collected by filtration and dried at 55° C. under vacuum for 4 hours to give 0.5 g of product, purity 99.56%. Upon measurement, the X-ray powder diffractogram of the obtained sample is consistent with that of Form A-I of salt of Formula A obtained in Example 1.

EXAMPLE 16

Preparation of Form A-I of Salt of Formula A (S)-7-(4-(1-(methylsulfonyl)piperidin-4-yl)phenyl)-N-(morpholin-2-ylmethyl)pyrido[3,4-b] pyrazin-5-amine (48 mg, 0.1 mmol) was suspended in 1 mL of methanol, and heated to 70° C. Then 0.2 mL of 1M acetic acid aqueous solution was added to obtain a clear solution. Then the reaction system was cooled to room temperature and stirred overnight. Then the precipitate was collected by filtration and dried to give 30.2 mg of product. Upon measurement, the X-ray powder diffractogram of the obtained sample is consistent with that of Form A-I of salt of Formula A obtained in Example 1.

EXAMPLE 17

Preparation of Form A-I of Salt of Formula A (S)-7-(4-(1-(methylsulfonyl)piperidin-4-yl)phenyl)-N-(morpholin-2-ylmethyl)pyrido[3,4-b] pyrazin-5-amine (1.5 g, 3.11 mmol) and 0.37 g of glacial acetic acid were suspended in a mixed solvent consisting of 6 mL of acetone and 3 mL of water, and heated to 50° C. After stirring at 50° C. for 20 minutes, 27 mL of acetone was added slowly. Then the mixture was heated to 60° C. and stirred for 2 hours, after which the mixture was cooled naturally to room temperature and stirred overnight. Then the precipitate was collected by filtration and dried to give 1.4 g of product, purity 99.72%. Upon measurement, the X-ray powder diffractogram of the obtained sample is consistent with that of Form A-I of salt of Formula A obtained in Example 1.

EXAMPLE 18

Preparation of Form B-I of Salt of Formula A (S)-7-(4-(1-(methylsulfonyl)piperidin-4-yl)phenyl)-N-morpholin-2-ylmethyl)pyrido[3,4-b] pyrazin-5-amine (1.0 g, 2.1 mmol) was suspended in a mixed solvent consisting of 30 mL of i-propanol and 4.6 mL of water, and heated to 80-85° C. under stirring. Then 2.3 mL of 1M p-toluenesulfonic acid aqueous solution was added. After dissolving completely, the reaction system was cooled to 15-20° C. and stirred for another 16 hours. Then the precipitate was collected by filtration and dried to give 1.06 g of product.

$^1$H NMR (400 MHz, dmso) δ 8.03-7.99 (m, J=2.0 Hz, 1H), 7.76-7.73 (m, J=2.0 Hz, 1H) 7.18-7.11 (m, J=8.4 Hz, 2H), 7.06-6.99 (m, J=6.0 Hz, 1H), 6.58-6.55 (m, 1H), 6.47-6.42 (m, 2H), 6.41-6.36 (m, J=8.4 Hz, 2H), 6.10-6.05 (m, J=7.8 Hz, 2H), 3.13-3.04 (m, 1H), 3.04-2.96 (m, J=12.5, 3.2 Hz, 1H), 2.83-2.64 (m, 7H), 2.18-2.11 (m, J=12.2 Hz, 1H), 2.08-1.96 (m, J=12.5, 8.7 Hz, 1H), 1.89 (s, 3H), 1.86-1.78 (m, J=12.0, 9.6 Hz, 3H), 1.74-1.66 (m, J=12.0 Hz, 1H), 1.25 (s, 3H), 0.94-0.85 (m, J=12.6 Hz, 2H), 0.77-0.64 (m, 2H).

The obtained powder sample is Form B-I of salt of Formula A, the X-ray powder diffractogram of which is shown in FIG. 4. Peaks (2θ) chosen from the figure have the following values: 4.9, 5.5, 6.8, 9.6, 10.1, 14.4, 14.8, 15.9, 16.4, 17.3, 18.4, 19.3, 19.8, 20.7, 21.4, 22.5, 23.2, 25.0, 26.1, 27.0, and 29.0 degrees, the measured 2θ values each having an error of about ±0.2 degrees (2θ), wherein characteristic peaks (2θ) are at 4.9, 5.5, 9.6, 14.4, 16.4, and 19.8 degrees. DSC result is given in FIG. 5, showing that the endothermic peak of Form B-I is at about 205.7-209.6° C.

EXAMPLE 19

Preparation of Form B-I of Salt of Formula A (S)-7-(4-(1-(methylsulfonyl)piperidin-4-yl)phenyl)-N-morpholin-2-ylmethyl)pyrido[3,4-b] pyrazin-5-amine (48 mg, 0.1 mmol) was suspended in 1.5 mL of 95% ethanol at 80° C. Then 0.11 mL of 1M p-toluenesulfonic acid aqueous solution was added to obtain a clear solution. After cooling to 15-20° C., the reaction system was stirred for another 3 hours. Then the precipitate was filtered out and dried to give the product. Upon measurement, the X-ray powder diffractogram of the obtained sample is consistent with that of Form B-I of salt of Formula A obtained in Example 18.

EXAMPLE 20

Preparation of Form B-I of Salt of Formula A (S)-7-(4-(1-(methylsulfonyl)piperidin-4-yl)phenyl)-N-(morpholin-2-ylmethyl)pyrido[3,4-b] pyrazin-5-amine (100 mg, 0.21 mmol) was suspended in 1 mL of ethanol, and heated to reflux slightly under stirring. Then 0.23 mL of 1M p-toluenesulfonic acid aqueous solution was added to obtain a clear solution. Then heating was stopped, and oil was precipitated. Then 2 mL of ethanol was added, and the stirring was continued at room temperature for another 3 days. Then the precipitate was filtered out and dried to give 124.36 mg of solid. Upon measurement, the X-ray powder diffractogram of the obtained sample is consistent with that of Form B-I of salt of Formula A obtained in Example 18.

EXAMPLE 21

Preparation of Form B-I of Salt of Formula A (S)-7(4-(1-(methylsulfonyl)piperidin-4-yl)phenyl)-N-(morpholin-2-ylmethyl)pyrido[3,4-b] pyrazin-5-amine (100 mg, 0.21 mmol) was suspended in a mixed solvent consisting of 2 mL of ethanol and 0.23 mL of water, and heated to 80-90° C. Then 0.23 mL of 1M p-toluenesulfonic acid aqueous solution was added to obtain a clear solution. Then the solution was cooled to room temperature and stirred for another 16 hours. Then the precipitate was collected by filtration and dried at room temperature to give 85 mg of product. Upon measurement, the X-ray powder diffractogram of the obtained sample is consistent with that of Form B-I of salt of Formula A obtained in Example 18.

EXAMPLE 22

Preparation of Form B-I of Salt of Formula A

About 50 mg of sample of Form B-II of salt of Formula A was suspended in about 0.5 mL of 95% ethanol, and stirred at 20° C. for 4 days. Then the precipitate was collected by filtration to give the product. Upon measurement, the X-ray powder diffractogram of the obtained sample is consistent with that of Form B-I of salt of Formula A obtained in Example 18.

EXAMPLE 23

Preparation of Form B-I of Salt of Formula A (S)-7-(4-(1-(methylsulfonyl)piperidin-4-yl)phenyl)-N-(morpholin-2-ylmethyl)pyrido[3,4-b] pyrazin-5-amine (100 mg, 0.21 mmol) was suspended in 1 mL of i-propanol, and heated to reflux slightly under stirring. Then 0.23 mL of 1M p-toluenesulfonic acid aqueous solution was added to obtain a clear solution. Then heating was stopped, and oil was precipitated. Then 3 mL of i-propanol was added, and stirred at room temperature for another 3 days. Then the precipitate was filtered out and dried to give 131.92 mg of solid. Upon measurement, the X-ray powder diffractogram of the obtained sample is consistent with that of Form B-I of salt of Formula A obtained in Example 18.

EXAMPLE 24

Preparation of Form B-I of Salt of Formula A (S)-7-(4-(1-(methylsulfonyl)piperidin-4-yl)phenyl)-N-(morpholin-2-ylmethyl)pyrido[3,4-b] pyrazin-5-amine (100 mg, 0.21 mmol) was suspended in 1 mL of acetone, and heated to reflux slightly under stirring. Then 0.23 mL of 1M p-toluenesulfonic acid aqueous solution was added to obtain a clear solution. Then heating was stopped, and oil was precipitated. Then 4 mL of acetone was added, and stirred at room temperature for another 3 days. Then the precipitate was filtered out and dried to give 94.77 mg of solid. Upon measurement, the X-ray powder diffractogram of the obtained sample is consistent with that of Form B-I of salt of Formula A obtained in Example 18.

EXAMPLE 25

Preparation of Form B-II of Salt of Formula A (S)-7-(4-(1-(methylsulfonyl)piperidin-4-yl)phenyl)-N-(morpholin-2-ylmethyl)pyrido[3,4-b] pyrazin-5-amine (100 mg, 0.21 mmol) was suspended in 1 mL of methanol, and heated to reflux slightly under stirring. Then 0.23 mL of 1M p-toluenesulfonic acid aqueous solution was added to obtain a clear solution. Then heating was stopped, and oil was precipitated. Then 2 mL of methanol was added, and stirred at room temperature for another 3 days. Then the precipitate was filtered out and dried to give 71.66 mg of solid.

$^1$H MIR (400 MHz, cdcl3) δ 8.88 (d, J=1.9 Hz, 1H), 8.57 (d, J=1.9 Hz, 1H), 8.07 (d, J=8.4 Hz, 2H), 7.65 (d, J=8.2 Hz, 2H), 7.55 (s, 1H), 7.31 (d, J=8.3 Hz, 2H), 7.07 (d, J=7.9 Hz, 2H), 6.95 (t, J=6.0 Hz, 1H), 4.21-4.12 (m, 1H), 4.04-3.88 (m, 6H), 3.47 (dd, J=42.8, 12.1 Hz, 2H), 3.12-3.03 (m, 1H), 2.98 (t, J=11.8 Hz, 1H), 2.83 (s, 3H), 2.80-2.75 (m, 2H), 2.71-2.62 (m, 1H) 2.28 (s, 3H), 1.98 (d, J=12.4 Hz, 2H), 1.92-1.84 (m, 2H).

The obtained powder sample is Form B-II of salt of Formula A, the X-ray powder diffractogram of which is shown in FIG. 7. Peaks (2θ) chosen from the figure have the following values: 5.1, 6.0, 9.5, 10.2, 14.3, 14.8, 15.3, 15.8, 17.1, 17.9, 19.1, 19.7, 20.2, 20.8, 22.4, 23.4, 26.0, and 27.2 degrees, the measured 2θ values each having an error of about 0.2 degrees (2θ), wherein characteristic peaks (2θ) are at 5.1, 6.0, 10.2, 17.1, and 19.1 degrees. DSC result is given in FIG. 8, showing that the endothermic peak of Form B-II is at about 203.0-211.4° C.

EXAMPLE 26

Preparation of Form B-III of Salt of Formula A (S)-7-(4-(1-(methylsulfonyl)piperidin-4-yl)phenyl)-N-(morpholin-2-ylmethyl)pyrido[3,4-b] pyrazin-5-amine (48 mg, 0.1 mmol) was suspended in 2.5 mL of water at 80-85° C. Then 0.11 mL of 1M p-toluenesulfonic acid aqueous solution was added to obtain a clear solution. Then the solution was cooled to room temperature under stirring, and precipitate appeared. Then the precipitate was filtered out and dried to give the solid.

The obtained powder sample is Form B-III of salt of Formula A, the X-ray powder diffractogram of which is shown in FIG. 9. Peaks (2θ) chosen from the figure have the following values: 5.3, 5.9, 9.9, 10.7, 11.8, 13.6, 14.9, 15.6, 16.0, 17.6, 18.9, 20.0, 21.6, 22.8, 25.0, and 27.0 degrees, the measured 2θ values each having an error of about ±0.2 degrees (2θ), wherein characteristic peaks (2θ) are at 5.3, 5.9, 10.7, 13.6, and 15.6 degrees. DSC result is given in FIG. 10, showing that Form B-III has an exothermic peak at about 168.1-172.5° C., and an obvious endothermic peak at about 199.6-208.3° C.

EXAMPLE 27

Preparation of Form B-III of Salt of Formula A

About 50 mg of sample of Form B-I of salt of Formula A was suspended in 0.5 mL of water, and stirred at room temperature for 4 days. Then the precipitate was collected by filtration and dried at 60° C. under vacuum for 2 hours to give the product. Upon measurement, the X-ray powder diffractogram of the obtained sample is consistent with that of Form B-III of salt of Formula A obtained in Example 26.

EXAMPLE 28

Preparation of Form C-I of Salt of Formula A (S)-7-(4-(1-(methylsulfonyl)piperidin-4-yl)phenyl)-N-(morpholin-2-ylmethyl)pyrido[3,4-b] pyrazin-5-amine (96.5 mg, 0.2 mmol) was suspended in 3 mL of i-propanol, and heated to 80-85° C. under stirring. Then 0.3 mL of 1M malic acid aqueous solution and 1.8 mL of water were added, and the reaction system became a clear solution. Then the solution was cooled to room temperature and stirred overnight. Then the precipitate was collected by filtration and dried to give 97.7 mg of product.

$^1$H NMR (400 MHz, dmso) δ 9.03 (d, J=2.0 Hz, 1H), 8.77 (d, J=2.0 Hz, 1H), 8.17 (d, J=8.4 Hz, 2H), 7.98 (t, J=6.1 Hz, 1H), 7.58 (s, 1H), 7.41 (d, J=8.4 Hz, 2H), 4.07-3.94 (m, 3H), 3.91 (dd, J=9.8, 4.2 Hz, 1H), 3.78-3.61 (m, 8H), 3.07-2.66 (m, 14H), 2.33 (dd, =15.6, 4.2 Hz, 1H), 1.93 (d, J=13.2 Hz, 2H), 1.74 (dt, J=12.5, 8.9 Hz, 2H).

The obtained powder sample is Form C-I of salt of Formula A, the X-ray powder diffractogram of which is shown in FIG. 11. Peaks (2θ) chosen from the figure have the following values: 8.6, 10.8, 11.8, 13.5, 14.3, 15.5, 16.4, 17.2, 17.7, 18.1, 18.4, 19.5, 20.9, 22.2, 22.6, 23.8, 25.8, 26.7, 27.8, 29.2, 29.8, and 30.7 degrees, the measured 2θ values each having an error of about ±0.2 degrees (2θ), wherein characteristic peaks (2θ) are at 8.6, 14.3, 15.5, 19.5, and 22.2 degrees. DSC result is given in FIG. 12, showing that the endothermic peak of Form C-I is at about 211.1-214.9° C.

EXAMPLE 29

Preparation of Form C-I of Salt of Formula A (S)-7-(4-(1-(methylsulfonyl)piperidin-4-yl)phenyl)-N-(morpholin-2-ylmethyl)pyrido[3,4-b] pyrazin-5-amine (1.0 g, 2.1 mmol) was suspended in 20 mL of ethanol, and heated to 80° C. Then 3.1 mL of 1M malic acid aqueous solution was added, followed by 12 mL of water, and the reaction system became a clear solution. Then 3 mL of ethanol was added, after which the reaction system was cooled to 15-20° C. and stirred for another 14 hours. Then the precipitate was filtered out and dried at 60° C. under vacuum for 2 hours to give 1.03 g of product, purity 99.7%. Upon measurement, the X-ray powder diffractogram of the obtained sample is consistent with that of Form C-I of salt of Formula A obtained in Example 28.

EXAMPLE 30

Preparation of Form C-I of Salt of Formula A (S)-7-(4-(1-(methylsulfonyl)piperidin-4-yl)phenyl)-N-(morpholin-2-ylmethyl)pyrido[3,4-b] pyrazin-5-amine (96.5 mg, 0.2 mmol) was mixed with 7 mL of tetrahydrofuran, 0.7 mL of water, and 0.3 mL of 1M malic acid aqueous solution, and heated for dissolving to obtain a clear solution. Then the reaction system was cooled to 15-20° C., after which 5 mL of tetrahydrofuran was added and stirred for another 3 days. Then the precipitate was filtered out and dried to give 87.9 mg of product. Upon measurement, the X-ray powder diffractogram of the obtained sample is consistent with that of Form C-I of salt of Formula A obtained in Example 28.

EXAMPLE 31

Preparation of Form C-I of Salt of Formula A (S)-7-(4-(1-(methylsulfonyl)piperidin-4-yl)phenyl)-N-(morpholin-2-ylmethyl)pyrido[3,4-b] pyrazin-5-amine (96.5 mg, 0.2 mmol) was mixed with 5 mL of methanol, 3 mL of water, and 0.3 mL of 1M malic acid aqueous solution, and heated to 75-80° C. to obtain a clear solution. Then the reaction system was cooled slowly to 15-20° C. under stirring. Then the precipitate was filtered out and dried to give 104 mg of product. Upon measurement, the X-ray powder diffractogram of the obtained sample is consistent with that of Form C-I of salt of Formula A obtained in Example 28.

EXAMPLE 32

Preparation of Form C-I of Salt of Formula A (S)-7-(4-(1-(methylsulfonyl)piperidin-4-yl)phenyl)-N-(morpholin-2-ylmethyl)pyrido[3,4-b] pyrazin-5-amine (48 mg, 0.1 mmol) was suspended in 3 mL of ethanol, and a suspension of 14.8 mg of malic acid in 0.2 mL of ethanol was added. Then the reaction system was kept warm at 40° C. and stirred for 20 hours, and then cooled to room temperature under stirring. Then the precipitate was filtered out and dried to give about 40 mg of product. Upon measurement, the X-ray powder diffractogram of the obtained sample is consistent with that of Form C-I of salt of Formula A obtained in Example 28.

EXAMPLE 33

Preparation of Form C-II of Salt of Formula A (S)-7-(4-(1-(methylsulfonyl)piperidin-4-yl)phenyl)-N-(morpholin-2-ylmethyl)pyrido[3,4-b] pyrazin-5-amine (48 mg, 0.1 mmol) was mixed with 3.5 mL of water, 0.6 mL of acetonitrile, and 0.11 mL of 1M malic acid aqueous solution, and heated to 80-85° C. under stirring to dissolve. Then the reaction solution was cooled to room temperature and stirred for another 18 hours. Then the precipitate was filtered out and dried to give 35.2 mg of product.

$^1$H NMR (400 MHz, dmso) δ 9.02 (d, J=2.0 Hz, 1H), 8.77 (d, J=2.0 Hz, 1H), 8.17 (d, J=8.4 Hz, 2H), 7.89 (t, J=6.0 Hz, 1H), 7.57 (s, 1H), 7.42 (d, J=8.4 Hz, 2H), 3.89 (d, J=9.1 Hz, 2H), 3.84 (dd, J=10.8, 3.4 Hz, 1H), 3.80-3.63 (m, 5H), 3.56 (dd, J=23.4, 11.8 Hz, 2H), 3.08 (d, J=12.7 Hz, 1H), 2.92 (d, J=2.1 Hz, 4H), 2.85 (dd, J=12.2, 9.8 Hz, 5H), 2.70 (dt, J=22.5, 1.1.2 Hz, 3H), 2.46 (d, J=10.8 Hz, 1H), 2.31 (dd, J=15.6, 3.4 Hz, 1H), 1.93 (d, J=12.9 Hz, 2H), 1.74 (dt, J=12.2, 8.5 Hz, 2H).

The obtained powder sample is Form C-II of salt of Formula A, the X-ray powder diffractogram of which is shown in FIG. 14. Peaks (2θ) chosen from the figure have the following values: 5.3, 9.5, 10.0, 10.6, 11.3, 11.6, 12.4, 12.8, 13.6, 15.9, 17.0, 18.4, 20.0, 20.9, 21.6, 23.1, 24.9, 26.4, 26.9, and 28.3 degrees, the measured 2θ values each having an error of about 0.2 degrees (2θ), wherein characteristic peaks (2θ) are at 11.3, 11.6, 17.0, 20.0, 21.6, and 23.1 degrees. DSC result is given in FIG. 15, showing that the endothermic peaks of Form C-II are at about 70.2-90.4° C. and about 202.6-215.0° C.

EXAMPLE 34

Preparation of Form C-III of Salt of Formula A (S)-7-(4-(1-(methylsulfonyl)piperidin-4-yl)phenyl)-N-(morpholin-2-ylmethyl)pyrido[3,4-b] pyrazin-5-amine (1.0 g, 2.1 mmol) was mixed with 11 mL of ethanol, 41 mL of water, and 3.1 mL of 1M malic acid aqueous solution, and heated to 80° C. to dissolve. Then the reaction system was cooled slowly to 15-20° C., and continued to stir overnight. Then the precipitate was collected by filtration and dried to give 0.94 g of product, purity 99.7%.

$^1$H NMR (400 MHz, dmso) δ 9.02 (d, J=2.0 Hz, 1H), 8.76 (d, J=2.0 Hz, 1H), 8.16 (d, J=8.4 Hz, 2H), 7.90 (t, J=5.9 Hz, 1H), 7.57 (s, 1H), 7.41 (d, J=8.4 Hz, 2H), 3.90 (d, J=8.9 Hz, 2H), 3.84 (dd, J=10.7, 3.4 Hz, 1H), 3.80-3.65 (m, 5H), 3.62-3.54 (m, 2H), 3.10 (d, J=11.8 Hz, 2H), 2.98-2.79 (m, 7H), 2.78-2.65 (m, 2H), 2.46 (d, J=10.7 Hz, 1H), 2.31 (dd, J=15.6, 3.4 Hz, 1H), 1.92 (d, J=12.8 Hz, 2H), 1.74 (qd, J=12.6, 4.0 Hz, 2H).

The obtained powder sample is Form of salt of Formula A, the X-ray powder diffractogram of which is shown in FIG. 17. Peaks (2θ) chosen from the figure have the following values: 5.3, 10.6, 11.8, 12.8, 16.0, 17.0, 17.9, 18.6, 18.9, 20.3, 21.7, 22.5, 23.1, 25.2, 25.6, and 27.4 degrees, the measured 2θ values each having an error of about 0.2 degrees (2θ), wherein characteristic peaks (2θ) are at 5.3, 10.6, 17.0, 17.9, and 25.2 degrees. DSC result is given in FIG. 18, showing that the endothermic peaks of Form C-III are at about 69.9-88.5° C. and about 201.6-206.7° C.

EXAMPLE 35

Stability Experiment of Salt of Formula A

Determination method: the test samples of Form A-I, Form B-I, Form C-I, and Form C-III of salt of Formula A were placed on the culture dishes respectively, which were uncovered and placed in sealed clean containers. The containers were placed under a temperature of 60° C. for 10 days, under an illumination of 4500lx±500lx for 10 days, and under a temperature of 25° C. and a relative humidity of 92.5%±5% for 10 days respectively. Then sampled on the 5$^{th}$ day and the 10$^{th}$ day respectively. Investigated for the purity (using HPLC analysis) and crystalline form (using X-ray powder diffraction analysis) of the samples, and compared the investigation results. The experimental results of the salts and the crystalline forms thereof were shown in Table 1, Table 2, Table 3, and Table 4.

TABLE 1

Results of Stability experiments of Form A-I of salt of Formula A

| Salt of Formula A (n is 1, M is acetic acid) | | Form | Purity (%) | Chiral Purity (%) |
|---|---|---|---|---|
| | 0 day | A-I | 99.39 | 99.63 |
| High temperature (60° C.) | 5 days | A-I | 99.31 | 99.66 |
| | 10 days | A-I | 99.37 | 99.71 |
| High humidity (92.5% RH) | 5 days | A-I | 99.35 | 99.69 |
| | 10 days | A-I | 99.53 | 99.71 |
| Illumination (4500 Lx) | 5 days | A-I | 99.30 | 99.69 |
| | 10 days | A-I | 98.99 | 99.71 |

TABLE 2

Results of Stability experiments of Form B-I of salt of Formula A

| Salt of Formula A (n is 1, M is p-toluenesulfonic acid) | | Form | Purity (%) | Chiral Purity (%) |
|---|---|---|---|---|
| | 0 day | B-I | 99.49 | 99.71 |
| High temperature | 5 days | B-I | 99.48 | 99.70 |
| (60° C.) | 10 days | B-I | 99.51 | 99.76 |
| High humidity | 5 days | B-I | 99.47 | 99.76 |
| (92.5% RH) | 10 days | B-I | 99.63 | 99.71 |
| Illumination | 5 days | B-I | 99.19 | 99.76 |
| (4500 Lx) | 10 days | B-I | 99.05 | 99.72 |

TABLE 3

Results of Stability experiments of Form C-I of salt of Formula A

| Salt of Formula A (n is 1, M is malic acid) | | Form | Purity (%) | Chiral Purity (%) |
|---|---|---|---|---|
| | 0 day | C-I | 99.71 | 99.52 |
| High temperature | 5 days | C-I | 99.61 | 99.52 |
| (60° C.) | 10 days | C-I | 99.63 | 99.54 |
| High humidity | 5 days | C-I | 99.72 | 99.53 |
| (92.5% RH) | 10 days | C-I | 99.68 | 99.53 |
| Illumination | 5 days | C-I | 99.67 | 99.51 |
| (4500 Lx) | 10 days | C-I | 99.61 | 99.50 |

TABLE 4

Results of Stability experiments of Form C-III of salt of Formula A

| Salt of Formula A (n is 0.5, M is malic acid) | | Form | Purity (%) | Chiral Purity (%) |
|---|---|---|---|---|
| | 0 day | C-III | 99.75 | 99.39 |
| High temperature | 5 days | C-III | 99.57 | 99.40 |
| (60° C.) | 10 days | C-III | 99.70 | 99.39 |
| High humidity | 5 days | C-III | 99.67 | 99.39 |
| (92.5% RH) | 10 days | C-III | 99.69 | 99.38 |
| Illumination | 5 days | C-III | 99.59 | 99.37 |
| (4500 Lx) | 10 days | C-III | 99.65 | 99.40 |

Conclusion: the data in Table 1, Table 2, Table 3, and Table 4 illustrate that, the chemical purity and crystalline forms of Form A-I, Form B-I, Form C-I, and Form of salt of Formula A are not changed after placed under high temperature for 10 days, under illumination for 10 days, or under high humidity condition for 10 days, showing that Form A-I, Form B-I, Form C-I, and Form C-III of salt of Formula A are stable.

EXAMPLE 36

Solubility Test of Salt of Formula A (1) Solubility test of salt of Formula A (acetate, Form A-I): an appropriate amount of sample of salt of Formula A (acetate, Form A-I) and an appropriate amount of sample of its free base (compound (S)-7-(4-(1-(methylsulfonyl)piperidin-4-yl)phenyl)-N-(morpholin-2-ylmethyl) pyrido[3,4-b]pyrazin-5-amine) were added into different solvents respectively, and stirred at certain temperature for 4 hours. Then the excess solids were filtered out, and the clear filtrates were used to determine solubility. The results were shown in Table 5.

TABLE 5

| | | Solubility (mg/mL) | |
|---|---|---|---|
| Dissolution Media | Test temperature | Free base of Formula A | Salt of Formula A (acetate, Form A-I) |
| Purified Water | 37° C. | 0.0025 | 26.15 |
| Purified Water | Room temperature | 0.0024 | 21.83 |
| Methanol | Room temperature | 1.58 | 7.11 |
| Ethanol | Room temperature | 0.64 | 2.04 |
| Tetrahydrofuran | Room temperature | 10.66 | 5.58 |
| Acetone | Room temperature | 2.12 | 2.53 |

Conclusion: the data in Table 5 illustrate that, the water solubility of salt of Formula A (acetate, Form A-I) is significantly higher than that of its free base.

(2) Rough solubility test of salt of Formula A: salt of Formula A, the rough solubility of which needed to be determined, was preweighed and added into a test tube. Then to the tube water was added dropwise in batches, and the amount of water added each time was recorded. After each addition of water, the test tube was shaken for 5 minutes until the solid was dissolved completely. Then the rough solubility of the compound was calculated according to the weight of the compound weighed and the total amount of water added. The calculated results were shown in Table 6.

TABLE 6

| Dissolution Media | Test temperature | Salt of Formula A | Rough solubility (mg/mL) |
|---|---|---|---|
| Purified Water | 19° C. | Acetate (Form A-I) | 14.6 |
| Purified Water | 19° C. | p-Tosylate (Form B-I) | 0.65 |
| Purified Water | 19° C. | Malate (Form C-I) | 0.48 |

Conclusion: the data in Table 6 combined with the data in Table 5 illustrate that, the water solubilities of salts of Formula A are all increased to some extent compared with its free base, wherein the solubility of acetate is significantly improved, followed by p-Tosylate and malate.

It is to be understood that, the examples and embodiments described herein are only for interpretation purposes, and various improvements or modifications in view of these would be suggested to those skilled in the art and are within the spirit and scope of present application and the scope of the appended claims. All the publications, patents and patent applications cited herein are incorporated herein by reference for all purposes.

What is claimed:

1. Salt of (S)-7-(4-(1-(methylsulfonyl)piperidin-4-yl)phenyl)-N-(morpholin-2-ylmethyl)pyrido[3,4-b]pyrazin-5-amine, which is acetate, p-Tosylate or malate salt.

2. The salt of claim 1, wherein said salt is monoacetate.

3. The salt of claim 1, wherein said salt is mono p-Tosylate.

4. The salt of claim 1, wherein said salt is monomalate.

5. The salt of claim 1, wherein said salt is hemimalate.

6. The salt of claim 2, being Form A-I, characterized in that the X-ray powder diffractogram of Form A-I has the characteristic peaks at the following 2-theta values: 6.2, 9.4, 16.3, 17.2, and 19.0 degrees, the measured 2θ values each having an error of about ±0.2 degrees (2θ), preferably wherein the X-ray powder diffractogram of Form A-I has the characteristic peaks at the following 2-theta values: 6.2, 9.4, 10.8, 16.3, 17.2, 19.0, 20.1, 21.7, 24.6, and 29.2 degrees, the measured 2θ values each having an error of about ±0.2 degrees (2θ).

7. The salt of claim 3, being Form B-I or Form B-II, characterized in that, the X-ray powder diffractogram of Form B-I has the characteristic peaks at the following 2-theta values: 4.9, 5.5, 9.6, 14.4, 16.4, and 19.8 degrees, the measured 2θ values each having an error of about ±0.2 degrees (2θ); the X-ray powder diffractogram of Form B-II has the characteristic peaks at the following 2-theta values: 5.1, 6.0, 10.2, 17.1, and 19.1 degrees, the measured 2θ values each having an error of about ±0.2 degrees (2θ).

8. The salt of claim 3, being a solvate, wherein said solvate is hydrate, preferably hemihydrate.

9. The salt of claim 8, characterized in that said hemihydrate is Form B-III, the X-ray powder diffractogram of Form B-III having the characteristic peaks at the following 2-theta values: 5.3, 5.9, 10.7, 13.6, and 15.6 degrees, the measured 2θ values each having an error of about ±0.2 degrees (2θ).

10. The salt of claim 4, being Form C-I, characterized in that the X-ray powder diffractogram of Form C-I has the characteristic peaks at the following 2-theta values: 8.6, 14.3, 15.5, 19.5, and 22.2 degrees, the measured 2θ values each having an error of about ±0.2 degrees (2θ).

11. The salt of claim 5, being solvate, wherein said solvate is hydrate, preferably wherein said hydrate is hydrate containing 0.75 molecule of water or is monohydrate.

12. The salt of claim 11, characterized in that, said hydrate containing 0.75 molecule of water is Form C-II, the X-ray powder diffractogram of Form C-II having the characteristic peaks at the following 2-theta values: 11.3, 11.6, 17.0, 20.0, 21.6, and 23.1 degrees, the measured 2θ values each having an error of about ±0.2 degrees (2θ); said monohydrate is Form C-III, the X-ray powder diffractogram of Form C-III having the characteristic peaks at the following 2-theta values: 5.3, 10.6, 17.0, 17.9, and 25.2 degrees, the measured 2θ values each having an error of about ±0.2 degrees (2θ).

13. A pharmaceutical composition, characterized in that it comprises an effective amount of one or more of salts of claim 1 and the pharmaceutically acceptable carriers.

14. A method of treating diseases associated with Syk kinase activity, such as autoimmune diseases, inflammatory diseases, and cancer (preferably hematological malignancy), comprising administering to a subject in need thereof an effective amount of the salts of claim 1, wherein said autoimmune diseases, inflammatory diseases, and cancer are selected from e.g., systemic lupus erythematosus, rheumatoid arthritis, Sjorgen's syndrome, IgA nephropathy, autoimmune hemolytic anemia, idiopathic thrombocytopenic purpura, multiple sclerosis, myasthenia gravis, allergic rhinitis, chronic obstructive pulmonary disease, adult respiratory distress syndrome, asthma, lymphoma (such as B cell lymphoma, T cell lymphoma), leukemia (such as chronic lymphocytic leukemia, acute lymphocytic leukemia, and acute myeloid leukemia), and multiple myeloma.

15. A method of preparing the salt of claim 6, said salt being Form A-I, comprising:
(1) reacting the compound (S)-7-(4-(1-(methylsulfonyl)piperidin-4-yl)phenyl)-N-(morpholin-2-ylmethyl)pyrido[3,4-b]pyrazin-5-amine with acetic acid to form a salt, which is stirred in at least one dissolution solvent (such as $C_{1-6}$ alkanol, tetrahydrofuran, dioxane, haloalkane with less than three carbon atoms, acetone, butanone, or acetonitrile) or a mixed solvent consisting of water miscible organic solvent (such as acetone; $C_{1-6}$ alkanol, e.g. methanol, ethanol, or i-propanol; dioxane; or acetonitrile) and water;
(2) isolating to obtain the solid Form A-I of (S)-7-(4-(1-(methylsulfonyl)piperidin-4-yl)phenyl)-N-(morpholin-2-ylmethyl)pyrido[3,4-b]pyrazin-5-amine acetate;
(3) optionally drying the solid obtained in step (2), or comprising:
(1) adding the compound (S)-7-(4-(1-(methylsulfonyl)piperidin-4-yl)phenyl)-N-(morpholin-2-ylmethyl)pyrido[3,4-b]pyrazin-5-amine and acetic acid into an appropriate amount of at least one dissolution solvent (such as $C_{1-6}$ alkanol, e.g. ethanol or i-propanol; or dichloromethane) or of a mixed solvent consisting of water miscible organic solvent (such as $C_{1-6}$ alkanol, e.g. methanol, ethanol, or i-propanol; dioxane; acetone; or acetonitrile) and water, and reacting to form a salt, thereby obtaining the first solution;

(2) adding at least one anti-dissolution solvent (such as acetone, isopropyl ether, or methyl tert-butyl ether) into said first solution to obtain the second solution;

(3) isolating to obtain the solid Form A-I of (S)-7-(4-(1-(methylsulfonyl)piperidin-4-yl)phenyl)-N-(morpholin-2-ylmethyl)pyrido[3,4-b]pyrazin-5-amine acetate;

(4) optionally drying the solid obtained in step (3).

16. A method of preparing the salt of claim 7, wherein, when said salt is Form B-I, the method comprises:

(1) reacting the compound (S)-7-(4-(1-(methylsulfonyl)piperidin-4-yl)phenyl)-N-(morpholin-2-ylmethyl)pyrido[3,4-b]pyrazin-5-amine with p-toluenesulfonic acid to form a salt, which is stirred in a mixed solvent consisting of water miscible organic solvent (such as $C_{1-6}$ alkanol, e.g. ethanol or i-propanol; or acetone) and water;

(2) isolating to obtain the solid Form B-I of (S)-7-(4-(1-(methylsulfonyl)piperidin-4-yl) phenyl)-N-(morpholin-2-ylmethyl)pyrido[3,4-b]pyrazin-5-amine p-Tosylate;

(3) optionally drying the solid obtained in step (2);

or, alternatively stirring Form B-II of salt of Formula A in about 95% ethanol at the temperature of about 10-30° C. to obtain Form B-I, and when said salt is Form B-II, the method comprises:

(1) reacting the compound (S)-7-(4-(1-(methylsulfonyl)piperidin-4-yl)phenyl)-N-(morpholin-2-ylmethyl)pyrido[3,4-b]pyrazin-5-amine with p-toluenesulfonic acid to form a salt, which is stirred in a mixed solvent consisting of methanol and water;

(2) isolating to obtain the solid Form B-II of (S)-7-(4-(1-(methylsulfonyl)piperidin-4-yl)phenyl)-N-(morpholin-2-ylmethyl)pyrido[3,4-b]pyrazin-5-amine p-Tosylate;

(3) optionally drying the solid obtained in step (2).

17. A method of preparing the salt of claim 9, said salt being Form B-III, comprising:

(1) reacting the compound (S)-7-(4-(1-(methylsulfonyl)piperidin-4-yl)phenyl)-N-(morpholin-2-ylmethyl)pyrido[3,4-b]pyrazin-5-amine with p-toluenesulfonic acid to form a salt, which is stirred in water;

(2) isolating to obtain the solid Form B-III of (S)-7-(4-(1-(methylsulfonyl)piperidin-4-yl) phenyl)-N-(morpholin-2-ylmethyl)pyrido[3,4-b]pyrazin-5-amine p-Tosylate;

(3) optionally drying the solid obtained in step (2);

or, alternatively stirring Form B-I of salt of Formula A in water at the temperature of about 10-30° C., collecting the solid by filtration, and optionally drying to obtain Form B-III.

18. A method of preparing the salt of claim 10, said salt being Form C-I, comprising:

(1) reacting the compound (S)-7-(4-(1-(methylsulfonyl)piperidin-4-yl)phenyl)-N-(morpholin-2-ylmethyl)pyrido[3,4-b]pyrazin-5-amine with malic acid to form a salt, which is stirred in at least one dissolution solvent (such as $C_{1-6}$ alkanol, e.g. methanol, ethanol, or i-propanol; or tetrahydrofuran) or a mixed solvent consisting of water miscible organic solvent (such as $C_{1-6}$ alkanol, e.g. methanol, ethanol, or i-propanol; or tetrahydrofuran) and water;

(2) isolating to obtain the solid Form C-I of (S)-7-(4-(1-(methylsulfonyl)piperidin-4-yl)phenyl)-N-(morpholin-2-ylmethyl)pyrido[3,4-b]pyrazin-5-amine malate;

(3) optionally drying the solid obtained in step (2).

19. A method of preparing the salt of claim 12, wherein, when said salt is Form C-II, the method comprises:

(1) reacting the compound (S)-7-(4-(1-(methylsulfonyl)piperidin-4-yl)phenyl)-N-(morpholin-2-ylmethyl)pyrido[3,4-b]pyrazin-5-amine with malic acid to form a salt, which is stirred in a mixed solvent consisting of acetonitrile and water;

(2) isolating to obtain the solid Form C-II of (S)-7-(4-(1-(methylsulfonyl)piperidin-4-yl) phenyl)-N-(morpholin-2-ylmethyl)pyrido[3,4-b]pyrazin-5-amine malate;

(3) optionally drying the solid obtained in step (2), and when said salt is Form C-III, the method comprises:

(1) reacting the compound (S)-7-(4-(1-(methylsulfonyl)piperidin-4-yl)phenyl)-N-(morpholin-2-ylmethyl)pyrido[3,4-b]pyrazin-5-amine with malic acid to form a salt, which is stirred in a mixed solvent consisting of ethanol and water;

(2) isolating to obtain the solid Form C-III of (S)-7-(4-(1-(methylsulfonyl)piperidin-4-yl) phenyl)-N-(morpholin-2-ylmethyl)pyrido[3,4-b]pyrazin-5-amine malate;

(3) optionally drying the solid obtained in step (2).

20. A pharmaceutical composition, characterized in that it comprises a salt of claim 6, and a pharmaceutically acceptable carrier; wherein the content of other crystalline forms of the salt in said pharmaceutical composition is less than 50%, preferably less than 40%, preferably less than 30%, preferably less than 20%, preferably less than 10%, preferably less than 5%, or preferably less than 1%, by weight, based on the total weight of the forms.

21. A pharmaceutical composition, characterized in that it comprises a salt of claim 6, a pharmaceutically acceptable carrier, and one or more other therapeutically active compounds; wherein the content of other crystalline forms of the salt in said pharmaceutical composition is less than 50%, preferably less than 40%, preferably less than 30%, preferably less than 20%, preferably less than 10%, preferably less than 5%, or preferably less than 1%, by weight, based on the total weight of the forms.

* * * * *